(12) United States Patent
Keles

(10) Patent No.: US 7,780,445 B2
(45) Date of Patent: Aug. 24, 2010

(54) PALATAL EXPANSION DEVICE AND METHODS

(76) Inventor: Ahmet Ozlem Keles, 304 Newbury St., PMB #266, Boston, MA (US) 02115

( * ) Notice: Subject to any disclaimer, the term of this patent is extended or adjusted under 35 U.S.C. 154(b) by 0 days.

(21) Appl. No.: 11/748,903

(22) Filed: May 15, 2007

(65) Prior Publication Data

US 2007/0218416 A1    Sep. 20, 2007

Related U.S. Application Data

(63) Continuation-in-part of application No. PCT/US2006/018562, filed on May 15, 2006, which is a continuation-in-part of application No. 10/908,536, filed on May 16, 2005, now Pat. No. 7,074,036.

(51) Int. Cl.
*A61C 3/00* (2006.01)
(52) U.S. Cl. .................. 433/24; 433/7; 433/18
(58) Field of Classification Search .............. 433/7, 433/18, 140
See application file for complete search history.

(56) References Cited

U.S. PATENT DOCUMENTS

| | | | |
|---|---|---|---|
| 3,835,540 A | | 9/1974 | Biederman |
| 4,045,817 A | * | 8/1977 | Nakatani et al. ............ 348/304 |
| 4,571,177 A | | 2/1986 | Dahan |
| 4,917,601 A | | 4/1990 | Williams |
| 4,991,566 A | * | 2/1991 | Shulman et al. ............. 600/213 |
| 5,281,133 A | * | 1/1994 | Farzin-Nia ..................... 433/7 |
| 5,472,344 A | | 12/1995 | Binder et al. |
| 5,975,894 A | | 11/1999 | Pozzi |
| 6,139,316 A | | 10/2000 | Sachdeva et al. |
| 6,626,665 B1 | | 9/2003 | Keles |
| 6,976,838 B1 | | 12/2005 | Keles |
| 7,074,036 B1 | | 7/2006 | Keles |
| 2003/0049581 A1 | * | 3/2003 | DeLuke .......................... 433/7 |
| 2003/0207225 A1 | | 11/2003 | Huge et al. |
| 2004/0152033 A1 | | 8/2004 | Collins |

FOREIGN PATENT DOCUMENTS

| | | |
|---|---|---|
| DE | 29501405 U1 | 3/1995 |
| FR | 2169540 A | 9/1973 |
| FR | 2193322 A | 2/1974 |

OTHER PUBLICATIONS

OrthoXpand, International Inc. Brochure, 2$^{nd}$ Generation RatchetRax (2004).

(Continued)

*Primary Examiner*—Cris L Rodriguez
*Assistant Examiner*—Yogesh Patel
(74) *Attorney, Agent, or Firm*—Antoinette G. Giugliano, PC

(57) ABSTRACT

The present invention embodies to a palatal expansion device that includes one or more stabilizers attached to the blocks; a ratchet that engages the screw; and a built-in activator that communicates with the ratchet. This design allows essentially unidirectional rotation of the screw. The ratchet system embodies a pin/pocket arrangement, or a ratchet wheel/spring arrangement. The present invention involves kits and methods for expanding the maxillary arch or mandible using the palatal expansion devices of the present invention.

18 Claims, 24 Drawing Sheets

OTHER PUBLICATIONS

OrthodonticProducts, Product Catalog, Novicom, Inc, pp. 35, (Jun. 2005).

OrthodonticProducts, Buyer's Guide 2005, Novicom, Inc, pp. 16-17, (Dec. 2004/Jan. 2005).

Biederman W.A., *J Pract Orthod*, Hygienic Appliance for Rapid Expansion 2:67-70 (1968).

Haas A.J., *Angle Orthod*, Rapid Expansion of the Maxillary Dental Arch and Nasal Cavity by Opening the Midpalatal Suture, 31:73-90 (1961).

Haas, A. J., *Am. J. of Orthodontics*, 57(3):219-255 (1970).

Wertz R.A., *Am J Orthod*, Skeletal and dental changes accompanying rapid midpalatal suture opening, 58:41-66 (1970).

Haas, A.J., *Angle Orthod*. The Treatment of Maxillary Deficiency by Opening the Midpalatal Suture;35:200-17 (1965).

Nazif, M.M. et al., *Journal of Dentistry for Children*, Accidental Swallowing of Orthodontic Expansion Appliance Keys: Report of Two Cases; 126-127 (Mar.-Apr. 1983).

\* cited by examiner

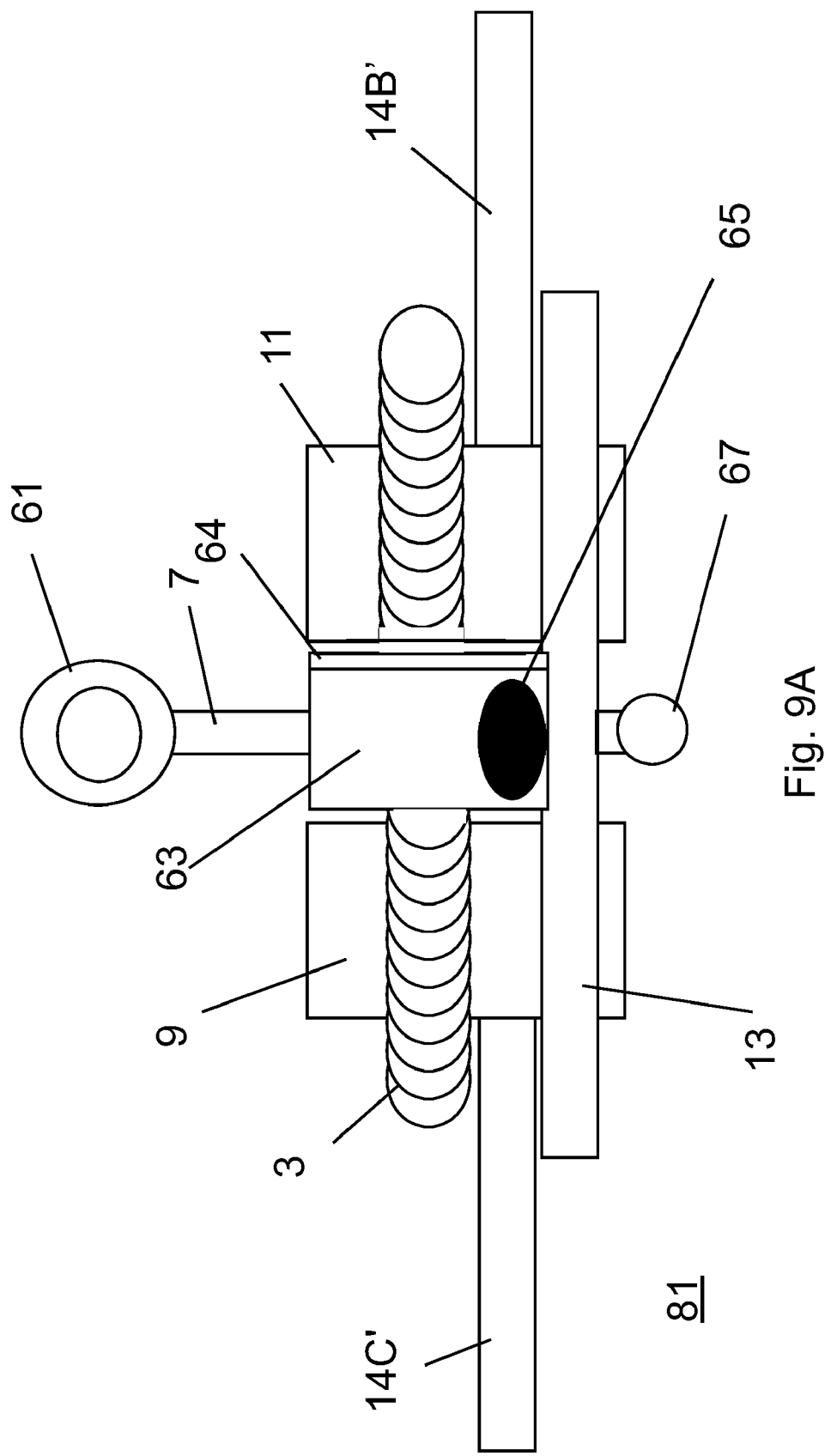

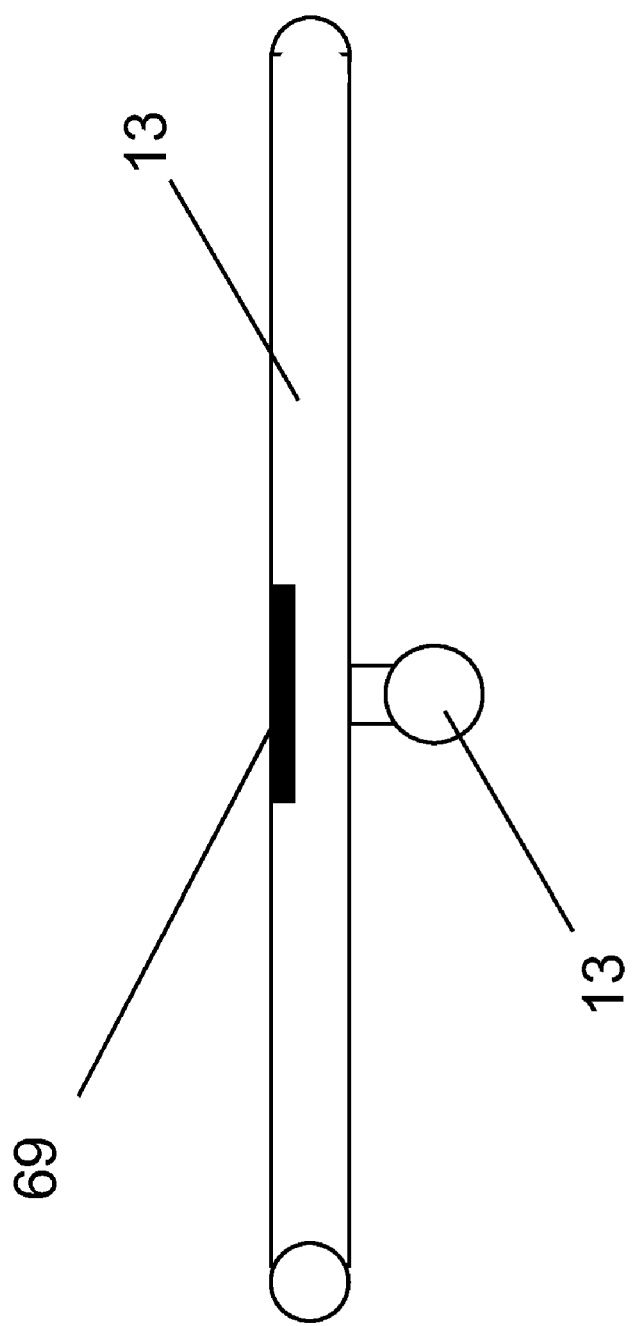

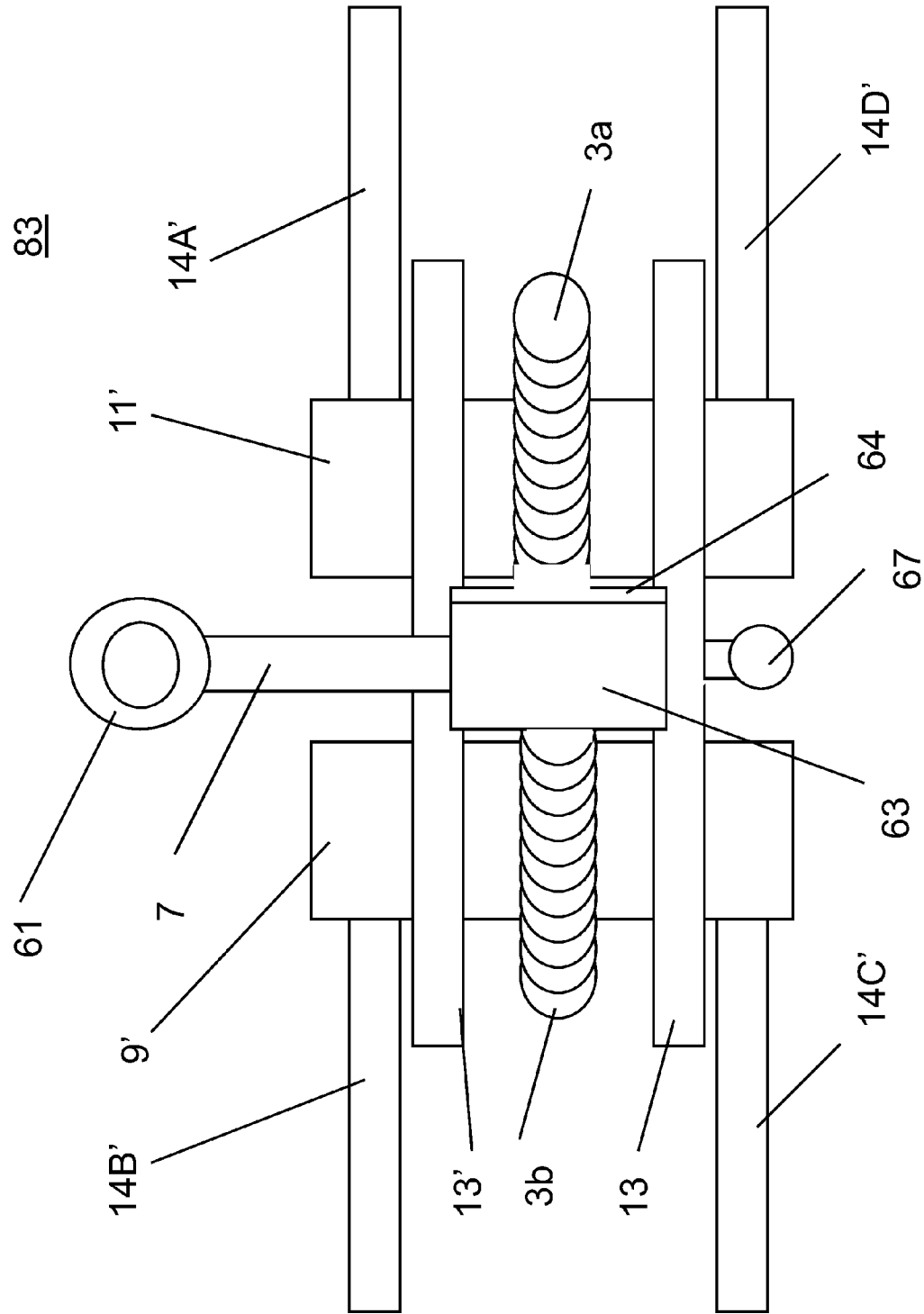

PALATAL EXPANSION DEVICE AND METHODS

RELATED APPLICATIONS

This application is a Continuation-In-Part of International Application No. PCT/US2006/018562, entitled, "Palatal Expansion Device and Methods," by Ahmet O. Keles which designated the United States and was filed May 15, 2006, published in English; which is a continuation-in-part of U.S. patent application Ser. No. 10/908,536, filed May 16, 2005, now issued as U.S. Pat. No. 7,074,036, entitled, "Palatal Expansion Device and Methods", by Ahmet O. Keles.

The entire teachings of the above applications are incorporated herein by reference.

BACKGROUND OF THE INVENTION

Constricted maxillary arch is often a significant dental and skeletal problem in field of orthodontics. Prior to the present invention, a fixed palatal expansion device generally consisted of a 4-band device with a midpalatal screw. In this example, the appliance had fixed bands on the maxillary first permanent molars and first premolars, connected on each side by a rigid bar, with both sides connected to each other by the screw. Such an appliance often consisted of 2 stabilizing bars, a screw with a hole in the middle for activation, and 2 metal blocks. These metal blocks are connected with each other by the screw and upon activation the blocks move apart from each other to achieve the transverse expansion of the upper jaw. In most instances, activation of the screw is performed by a pin shaped key. The appliance is initially cemented to the teeth and activated twice a day by the patient with the key until the desired expansion is achieved.

Looking at the above-described device from a clinical point of view, patients have a hard time finding the hole on the screw with the pin shaped key, inserting the key and turning the screw backwards in the direction of the throat by looking to an inverted image on a mirror. The hole on the screw is often very small; generally its diameter is less than a millimeter. Hence, even with the help of the pin shaped key, it is difficult to find. Furthermore, other risks exist. They include injuring the soft palate during insertion of the key and/or swallowing the key during activation. In some cases, accidental swallowing of orthodontic expansion appliance keys has been reported.

After the desired expansion is achieved, the activation of the screw is stopped and the appliance is maintained in the mouth for 3 months for stabilization and adaptation of the tissues. However during this time period, unwinding of the screw can happen thereby causing the blocks to retract, and some of the achieved expansion can be lost during the stabilization period.

Hence, a need exists for an effective palatal expander that is patient friendly. In particular, a need exists for a palatal expander that does not require a key, that is easy to use, and achieves the desired maxillary expansion without retraction of the device.

SUMMARY OF THE INVENTION

The present invention relates to a palatal expansion device that has a screw having an activation mechanism (e.g., one or more activation arms, or an activation wheel) wherein the screw connects two blocks, each block having an opening for receiving the screw; a stabilizer (e.g., one or more stabilizers) attached to the blocks; and an anti-wind-back mechanism (e.g., spring extension) positioned opposite the activation arms, wherein the anti-wind-back mechanism is attached to any component of the device (e.g., the stabilizer or one of the blocks). The device, in an embodiment, further includes two or more retaining wires (e.g., four wires) for securing the device to the teeth, wherein the wires are laterally attached to the blocks. In another embodiment, the device includes an acrylic composite or resin that connects the device to one or more clasps that are secured to one or more teeth. In one aspect, the screw perpendicularly transects the blocks at the opening. The anti-wind-back mechanism such as the spring extension is made, in an embodiment, from an alloy (e.g., nickel titanium alloy), a metal, a plastic, or rubber.

In another embodiment, the present invention pertains to a palatal expansion device that has two blocks; a means for separating the two blocks with an activation mechanism (e.g., one or more activation arms); a means for stabilizing the blocks (e.g., a stabilizer); and a self-locking or anti-wind-back mechanism (e.g., a spring extension) that engages the activation arm to thereby prevent retraction of the blocks. The means for stabilizing (e.g., a prism shaped bar, or cylindrical shaped rod) includes, in one embodiment, a rod securely attached to the blocks (e.g., welded, connected by clasps or bands, cemented). The embodiment further includes two or more retaining wires (e.g., four wires) for securing the appliance to teeth, wherein the wires are laterally attached to the blocks.

The present invention further embodies a palatal expansion device that has at least one screw, wherein the screw connects with one or more blocks, the block having an opening for receiving the screw; one or more stabilizers attached to the blocks; a (e.g., at least one) ratchet that engages the screw; and a (e.g., at least one) built-in activator (e.g., an activation arm) that communicates with the ratchet. The ratchet allows for essentially unidirectional rotation of the screw. In an embodiment, the ratchet comprises a pin, housing and one or more pockets (e.g., 3 pockets) to guide movement of the pin. The screw can have an opening to slidably receive the pin of the ratchet. The pin transects the screw at an opening in the screw. In another embodiment, the ratchet includes a spring opposite one or more projections of a ratchet wheel wherein the projections engage the spring to allow essentially unidirectional rotation of the screw. The present invention can further include a pull back device that engages the activation arm. The pull back device includes an elastic member (e.g., a spring coil, elastic thread, elastic chain, or combination thereof) attached to the activation arm, and an anchor (e.g., a hook, a structure of the device). An embodiment of the present invention further has a stopper, disposed on the housing, and in another aspect it includes two or more retaining wires (e.g., about 2 to about 4) for securing the appliance to teeth. These wires can be laterally attached to the blocks. One aspect of the present invention pertains to a screw that essentially perpendicularly transects the blocks at the opening. In an embodiment, the expander of the present invention allows the screw to move from a first position (e.g., starting position) to a second position (e.g., finishing position) and the screw is prevented from moving back to the first position.

The present invention further embodies a palatal expansion device that has about two blocks, a means for separating (e.g., a screw) the two blocks with a built-in activator; a means for stabilizing (e.g., a bar, a prism, or a rod) the blocks; and a ratchet means, as described herein, to thereby allow essentially unidirectional rotation of the screw and prevents retraction of said blocks. The palatal expansion device, in an embodiment, includes one or more acrylic plates, wherein a portion of the device is imbedded in the acrylic plate. The device can further include one or more clasps imbedded in said acrylic plate.

The present invention also includes methods of expanding a maxillary arch or a mandibular arch of a person. The methods include the steps of securing a palatal expansion device, as described herein and engaging the activator (e.g., activation arm) to thereby expand the arch or mandible. For rapid expansion, the activation mechanism can be engaged on a daily basis (e.g., once, twice, or three times a day), every other day, or every few days, depending on the extent of the expansion. The period of activation can be from about 1 week and about 2 weeks, or more (e.g., about 3 or 4 weeks). For a slower expansion, the activation mechanism is engaged once or twice a week for a period of between about 1 month and about 1 year (preferably between about 6 and 8 months). The period of activation can be followed by a period of stabilization. For rapid expansion, the stabilization period is generally between about 2 and about 4 months (e.g., an average of about 3 months), and for slow expansion is between about 10 months to about 1½ years (e.g. an average of about 1 year).

A kit for palatal expansion is further embodied by the present invention. The kit includes the palatal expansion device described herein and either an acrylic composition, or two or more retaining wires (e.g., four wires) for securing the device to teeth. The kit can additionally include additional items normally associated with securing or using such a device e.g., coil spring, elastic thread, an elastic chain, or combination thereof.

The present invention has several advantages. The device does not require a pin shaped key for activation of the screw because an activation arm is built-in into the device. The device of the present invention is safer because there is no risk of swallowing a pin shaped key or puncturing the soft palate during insertion of such a key. The built-in activation arm more easily allows for activation of the screw and is therefore more patient friendly. As such, greater patient compliance is obtained. Another advantage of the present invention is the built-in locking or ratchet (e.g., anti-wind-back) mechanism which prevents the screw from winding back after the desired expansion is achieved.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

FIG. 9A is a diagram showing a bird's eye view of an embodiment of the palatal expansion device having a ratchet system, one stabilizer and two retaining wires.

FIG. 11 is a diagram showing the top view of a stabilizer used in an embodiment of the palatal expansion device.

FIG. 14 is a diagram showing a bird's eye view of an embodiment of the palatal expansion device having a ratchet system, two stabilizer and four retaining wires.

DETAILED DESCRIPTION OF THE INVENTION

A description of preferred embodiments of the invention follows.

Figure 1:
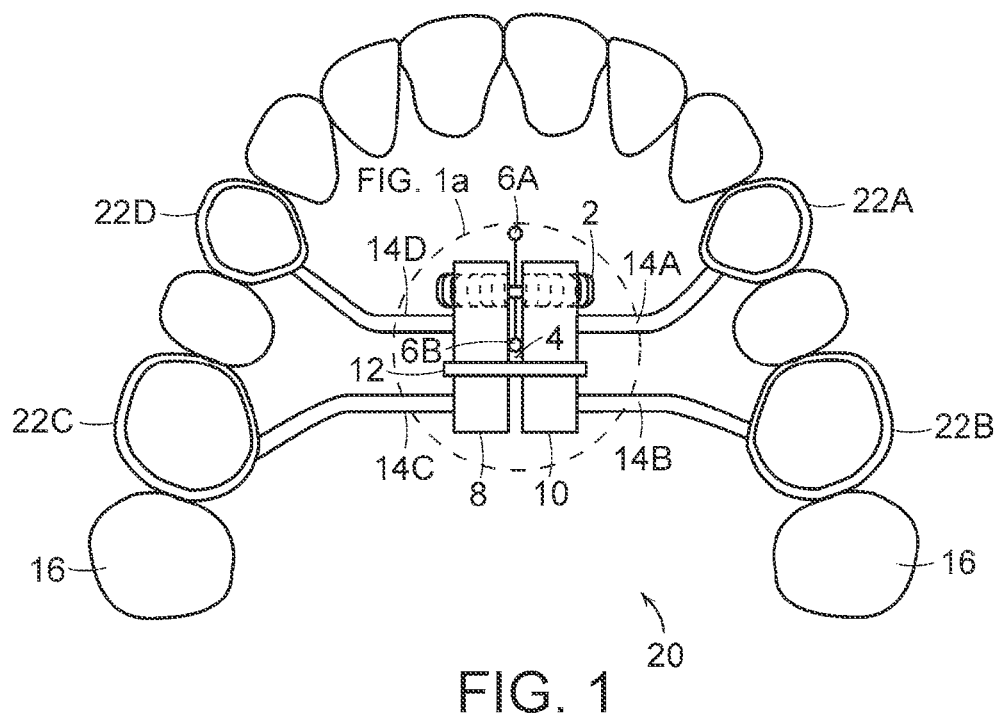
FIG. 1 is a diagram showing an embodiment of the palatal expansion device of the present invention secured to a maxillary arch.
Figure 3A:
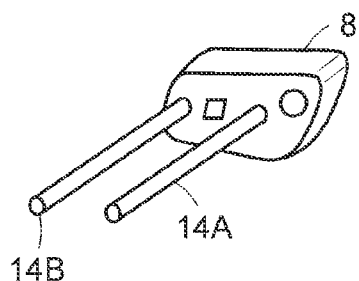
FIG. 3A is a diagram of a perspective view showing the outside of one block, two retaining wires, a square hole for receiving a stabilization bar, and a round hole for receiving the screw for one embodiment of the palatal expansion device of the present invention.
Figure 3C:
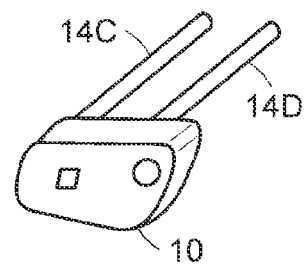
FIG. 3C is a diagram of a perspective view showing the inside of one block, two retaining wires, a square hole for receiving a stabilization bar, and a round hole for receiving the screw for an embodiment of the palatal expansion device of the present invention.

Referring to FIG. 1, palatal expansion device 20 is secured to maxillary arch 16 by bands 22A-22D and retaining wires 14A-14D. Palatal expansion device 20 has a mid-palatal screw 2 that separates blocks 8 and 10 to expand the upper jaw and dentition. In this embodiment, screw 2 has four prong-shaped activation arms, activation arms 6A-6D, that are securely attached to a middle portion of screw 2. A detailed view of screw 2 and activation arms 6A-6D are shown in this figure and in FIG. 3D. In addition to a screw, other means for separating the block can be use so long as the means is attached to an activation arm that can be engaged by the user and acts to separate the blocks, as described herein. Additionally, a combination of one or more screws can be used in place of a single screw. For example, two screws opposing each other can be used to push the blocks outward, connected by a metal connector to which the activation arms are secured. In one embodiment, turning an activation arm causes screw 2 to turn a ¼ of a turn. The number of activation arms and the tread of the screw can be adjusted to obtained the desired expansion distance for each activation. In one embodiment, a 2 mm screw, with 4 activation arms, causes the screw to achieve a 0.25 mm expansion. Similarly, in another embodiment, a screw with a smaller diameter, e.g., a 1 mm screw, with 2 activation arms, could also cause the screw to achieve the same 0.25 mm expansion. In an embodiment, the tread of the screw (e.g., the diameter of the screw) can range from between about 0.5 mm and about 4 mm, and the number of activation arms can range from 1 to 8 arms to obtain the desired expansion for each activation, and preferably between 1 and 4 arms. The present invention includes a device that expands, for each activation, between about 0.1 mm and about 0.4 mm, and preferably between about 0.2 mm and about 0.3 mm (e.g., about 0.25 mm).

The device can be used as a rapid palatal expander or a slow palatal expander. In the case of a rapid palatal expander, the period of activation is between about 1 week and about 2 weeks, or more (sometimes about 3 or 4 weeks) to obtain the maximum desired expansion. In the case of a slow palatal expander, the period of activation, in an embodiment, is between about 1 month to about 1 year. The device of the present invention can therefore achieve a maximum expansion between about 3 mm and about 15 mm, and preferably between 7 mm and about 11 mm (e.g., about 7 mm, about 9 mm or about 11 mm) The maximum range of expansion can be adjusted by lengthening or shortening the screw, and the stabilizing bars, as further described herein. The screw size can be selected based on the amount of expansion needed.

Figure 1A:
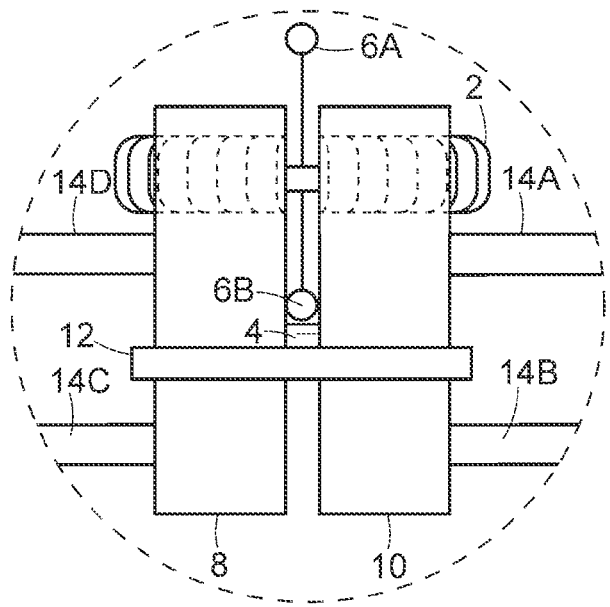
FIG. 1a is a detailed view of the palatal expansion device.
Figure 4:
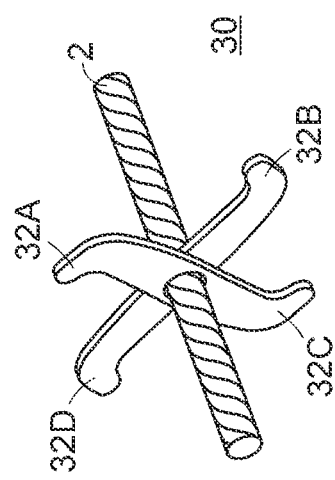
FIG. 4 is a diagram of a perspective view of another embodiment of the screw with four sprocket wheel activation arms of a palatal expansion device of the present invention.
Figure 5:
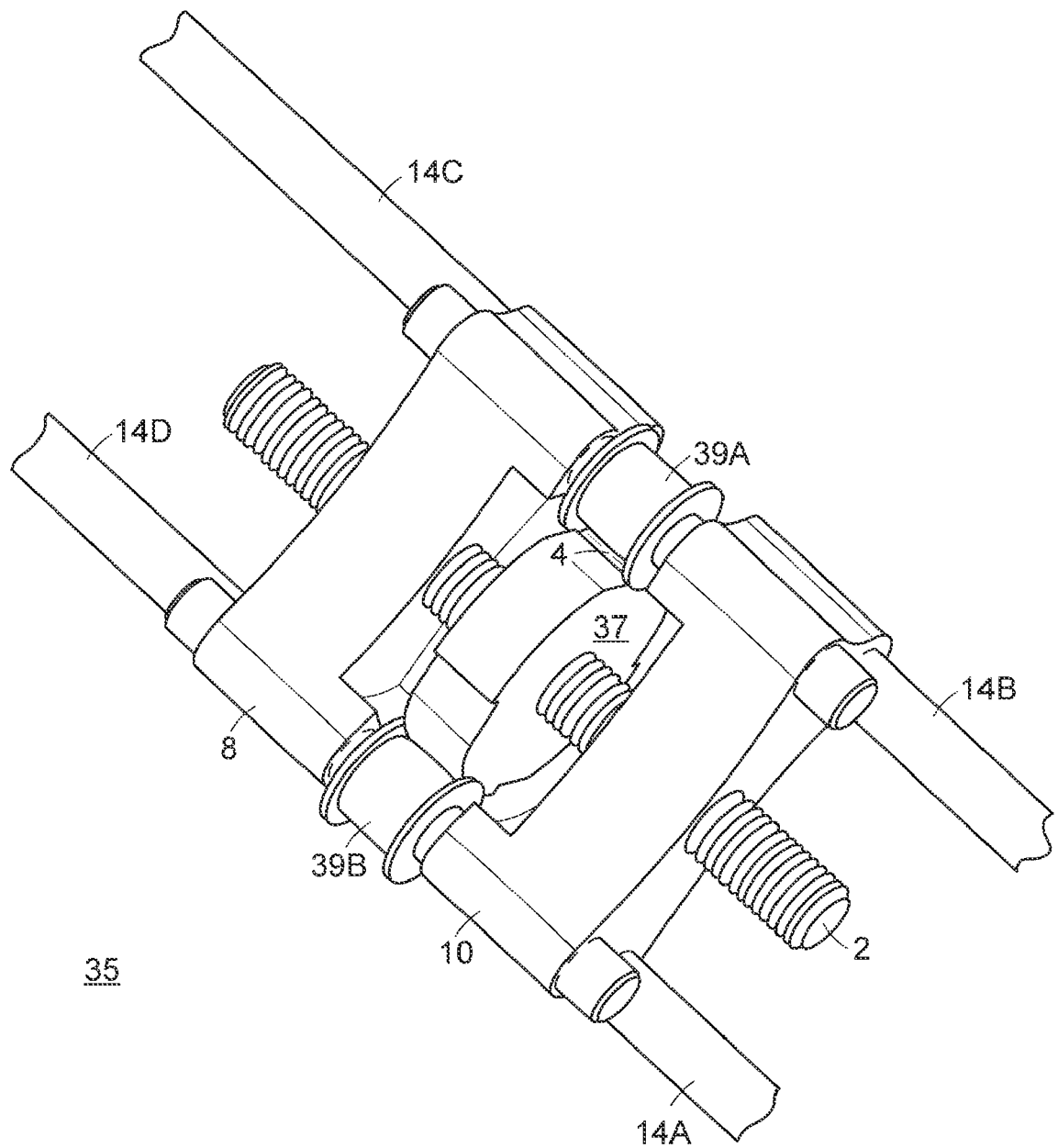
FIG. 5 is a diagram of a perspective view of another embodiment of the palatal expansion device of the present invention, wherein a wheel with indentations is used to activate the device.

FIGS. 1 and 1a show activation arms 6A-6D having a ball-shaped head on the end of each arm to more easily allow the patient to turn it. In addition to activation arms, any activation mechanism or activator can be used so long as the mechanism engages the screw without the use of a separate activation key or expansion key to achieve the desired expansion. "Activation mechanism" and "activator" are used interchangeably herein. With respect to the activation arm, its shape can be any shape, so long as the patient can engage the arm to turn it. The activator can be attached directly to the screw, or used to engage a ratchet system, as described further herein. Preferably, the end of the activation arm is shaped without sharp edges to avoid accidental puncturing by the tongue or finger. In one embodiment, the activation mechanism is the shape of a wheel, having evenly spaced indentations that are angled to aid in the patient's activation of the expansion device. This embodiment of the invention is further described herein and is shown in FIG. 5. In another embodiment shown in FIG. 4, the activation arms 32A-D are finger-like projections having an angled tip that engages an anti-wind-back mechanism. An anti-wind-back mechanism or device refers to a device that allows the screw to rotate in one direction, and/or prevents the screw to go back to a previous position. The embodiments shown in FIGS. 1 and 4 allow the activation arms and screw to work like a sprocket wheel. As shown in FIG. 9, the activator is an arm with a circular grip at the end and works together with a ratchet to achieve unidirectional rotation of the screw.

The built-in activation arm relinquishes the need for a pin-like key to turn the screw, and all the disadvantages associated with the use of such a key (e.g., trying to place the pin to the small hole of the screw to activate the screw, puncturing the soft palate, accidental swallowing of the key, losing the key, etc.).

Figure 3E:
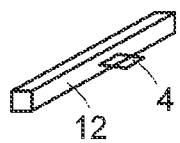
FIG. 3E is a diagram of a perspective view of the spring extension attached to the stabilization bar of an embodiment of the palatal expansion device of the present invention.
Figure 6:
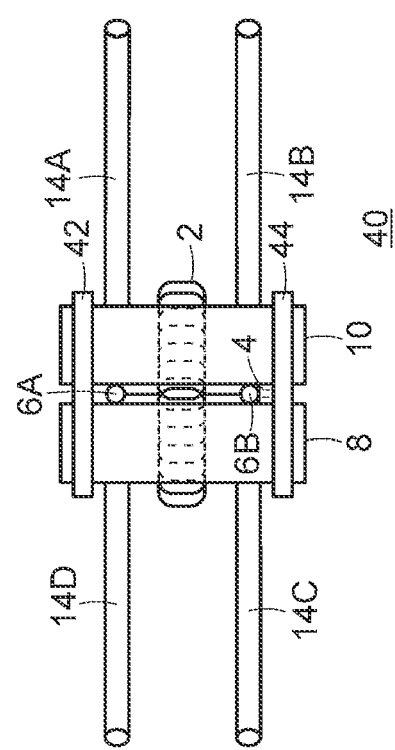
FIG. 6 is a diagram of a top view of another embodiment of the palatal expansion device of the present invention, wherein the device has two stabilizing bars.

Stabilizing bar 12 along with spring extension 4 are shown in FIG. 1, and in more detail in FIG. 3E. Stabilizing bar 12 is a square shaped prism which goes through the square shape holes of blocks 8 and 10. See FIGS. 3A and 3C. One or more (e.g., 1, 2, 3, or 4) stabilizing bars can be used. For example, FIGS. 5-8 show embodiments having two stabilizing bars. In the embodiments using a ratchet, FIG. 11 shows a single stabilizer, stabilizing rod 13, while FIG. 6 shows two stabilizing rods, stabilizing rod 13 and 13'. The holes transect blocks 8 and 10 to allow for stabilizing bar 12 to slide freely along the blocks during expansion. Stabilizing bars function to stabilize the device to keep the blocks moving along a straight axis, e.g., by preventing the blocks from swiveling during expansion. Any means for stabilizing the blocks can be used so long as the means keeps the blocks moving along essentially a straight axis and in the direction of expansion. In addition to a bar, the stabilizer can be of any shape and includes cylindrical shaped rods; or rectangular, square, or triangular shaped prisms. The stabilizer in FIG. 1 uses a bar while the stabilizer in FIG. 19A uses a rod. The stabilizing mechanism can be made from metal, plastic, rubber or any other material known in the art or later developed that can withstand the force of expansion.

Figure 2:
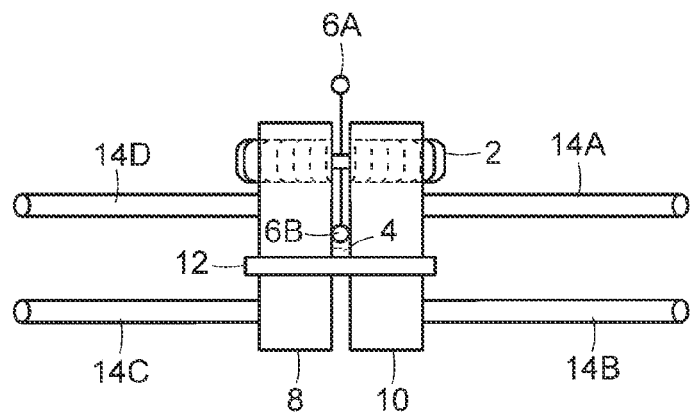
FIG. 2 is a diagram of a top view of another embodiment of the palatal expansion device of the present invention.
Figure 3B:
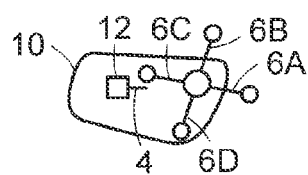
FIG. 3B is a diagram of a side view showing a spring extension attached to the stabilization bar and positioned opposite to four activation arms of an embodiment of the palatal expansion device of the present invention.
Figure 3D:
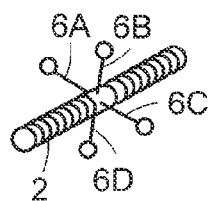
FIG. 3D is a diagram of a perspective view showing the screw and four activation arms attached to the screw for an embodiment of the palatal expansion device of the present invention.

Attached to stabilizing bar 12 is spring extension 4. Spring extension 4 acts as a self-locking or anti-wind-back mechanism for screw 2. FIGS. 1, 3B and 3E show spring extension 4 that looks like a plate projection that functions like a cog to lock the screw. The anti-wind-back mechanism, like spring extension 4, prevents screw 2 from winding back, which in turn prevents retraction of the blocks. The anti-wind-back mechanism can be any mechanism that allows the screw to pass in one direction, but does not allow for the screw to reverse direction or to prevent wind back of the screw. Allowing the screw to pass in one direction, in an embodiment, refers to the screw rotating unidirectional from a first position to a second position, and unable to go back to its previous position (e.g., the first position). Examples of an anti-wind-back mechanism include not only a spring extension, but also a wire extension, ratchets, or guides positioned to allow the activation mechanism to achieve expansion in one direction. An anti-wind-back mechanism can be positioned perpendicularly to one of the stabilizing bars, as is spring extension 4 to stabilizing bar 12, or at an angle (e.g., a slightly downward angle) to achieve unidirectional directional flow. The anti-wind-back mechanism can be attached to any component of the palatal expansion device. For example, the anti-wind-back mechanism can be attached to a stabilizing bar, as shown in FIGS. 1 and 2, to a block or any other component so long as its position engages the activation mechanism to prevent unwanted wind back. The spring extension or anti-wind-back mechanism can also have a rounded or cup-like shape, or other shape that complements the end of the activation arm. In an embodiment, the anti-wind back mechanism is a ratchet system and includes a pin & pocket arrangement, a wheel and plate arrangement, and other arrangements to achieve essentially unidirectional flow, as described further herein. The anti-wind-back mechanism including the spring extension or any other component of the device can be made from metal, alloy (e.g., nickel titanium alloy), plastic, rubber, wire, metal curtain or other suitable material that is known in the art or later developed.

Blocks 8 and 10 act as supports for device 20. Such blocks or supports can be made from metal, rubber, plastic or any other suitable material known in the art or later developed to act as supports for the expansion device of the present invention. Blocks 8 and 10 have an opening to receive screw 2. The opening used to receive the one or more screws of the device can extend partially, or along the entire width of one or both blocks. For example, in FIGS. 3A and C, the opening that receives screw 2 extends along the entire width of both blocks to allow screw 2 to extend past the end of each block. In this embodiment, both blocks move along the screw during expansion. In another embodiment, one block can have a screw opening that extends along the entire width of the screw, while the other block has a screw mounted to the block. During expansion, only one block, instead of two, moves along the screw, which in turn allows an equal expansion.

As shown in FIG. 1, blocks 8 and 10 also have an opening for receiving stabilization bar 12. The opening allows blocks 8 and 10 to slide along stabilization bar 12, as described herein. The stabilizers can be mounted to one or more of the blocks so that the blocks are allows to slide during expansion. The blocks (e.g., supports) can have as many openings as needed to accommodate one or more screw, stabilizers, or any other components. The supports can also be of any shape or size so long as it as they act to expand the palate. Additionally in the embodiment shown in FIGS. 1, 3A and 3C, blocks 8 and 10 accommodate retaining wires 14A-D. The device of the present invention, in an embodiment can have two or more retaining wires, and in other embodiments have four retaining wires. Retaining wires are used to secure the device to the maxillary arch or mandible. In one example, retaining wires can be secured to the molar and premolar bands. They project from the outside surfaces of the blocks and extend outward toward the molar and premolar bands. The device can also be secured to the maxillary arch or mandible with acrylic or other suitable material, as further described herein.

FIG. 2 shows device 20 when it is not secured to the maxillary arch. Retaining wires 14A-D are straight and can be soldered to the premolar and molar band, or bonded directly to the palatal side of the molar and premolar teeth. FIG. 2 shows one embodiment of the palatal expansion device of the present invention prior to being secured to a patient. The device can be provided with or without retaining wires. In the case where the device is not provided with retaining wires, the device has a point of attachment for the wires that can be threaded or attached by the orthodontist in the dental office.

Palatal expansion device 35, shown in FIG. 5, employs activation wheel 37 as an activation mechanism. Activation wheel 37 has indentations that complement stabilization guides 39A-B, the anti-wind-back mechanism. The present invention includes several embodiments that allow for activation independent of an expansion key while preventing wind-back. In this embodiment and as described herein, the activation mechanism and anti-wind-back mechanism complement each other and allow for a unidirectional movement of the screw. Numerous variations of activation mechanisms and complementing anti-wind-back mechanisms are encompassed by the invention.

As shown in FIG. 6, palatal expansion device 40 is similar to device 20 (FIG. 1), except that device 40 utilizes two stabilizing bars, stabilizing bars 42 and 44. Stabilizing bars 42 and 44 serve to further stabilize screw 2 to prevent expansion in an undesired direction. As described herein, the palatal expansion device of the present invention includes one or more stabilizers, sufficient to prevent skewing of the retraction blocks. Stabilizers can be of varying shape, width, size and weight.

Figure 7:
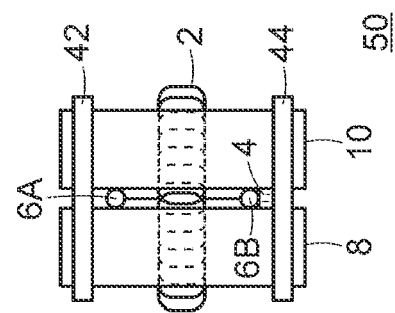
FIG. 7 is a diagram of a top view of yet another embodiment of the palatal expansion device of the present invention, wherein the device has no retaining wires attached to it.
Figure 8A:
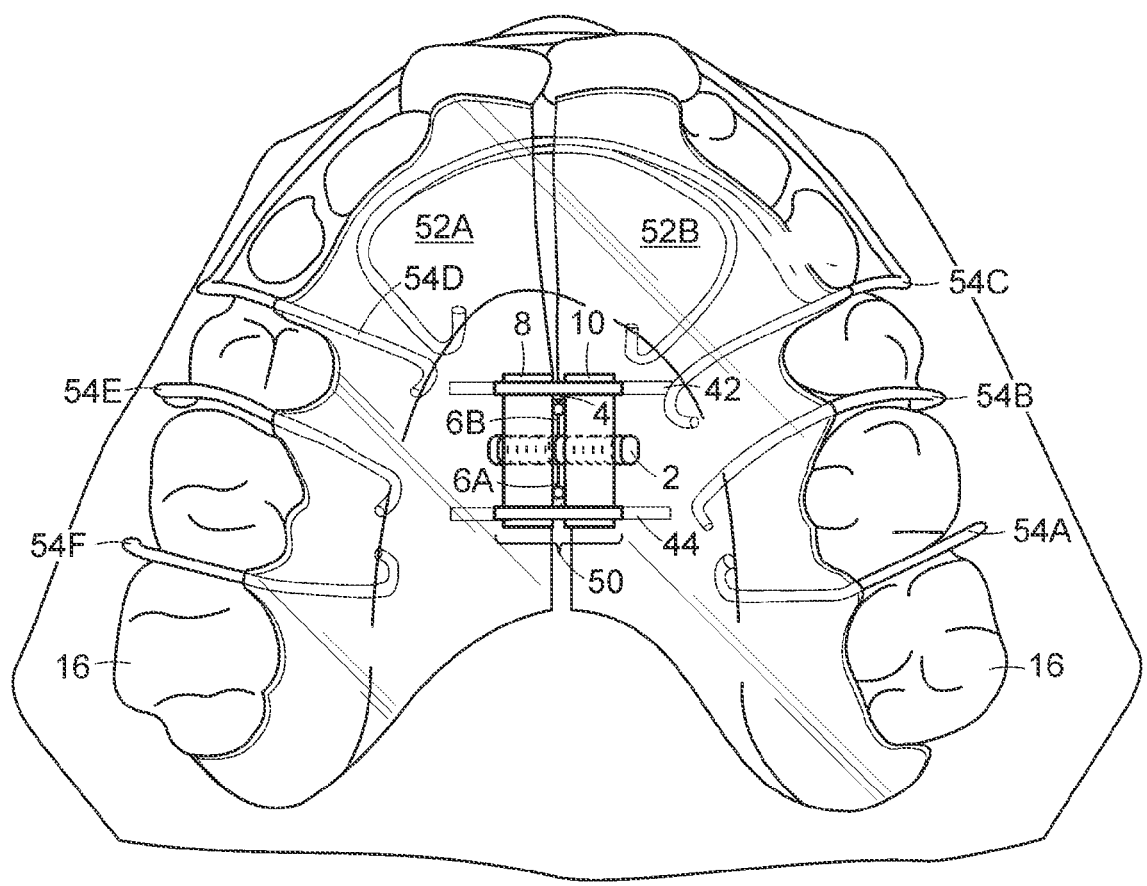
FIG. 8A is a diagram showing an embodiment of the palatal expansion device of the present invention removably secured to a maxillary arch.
Figure 8B:
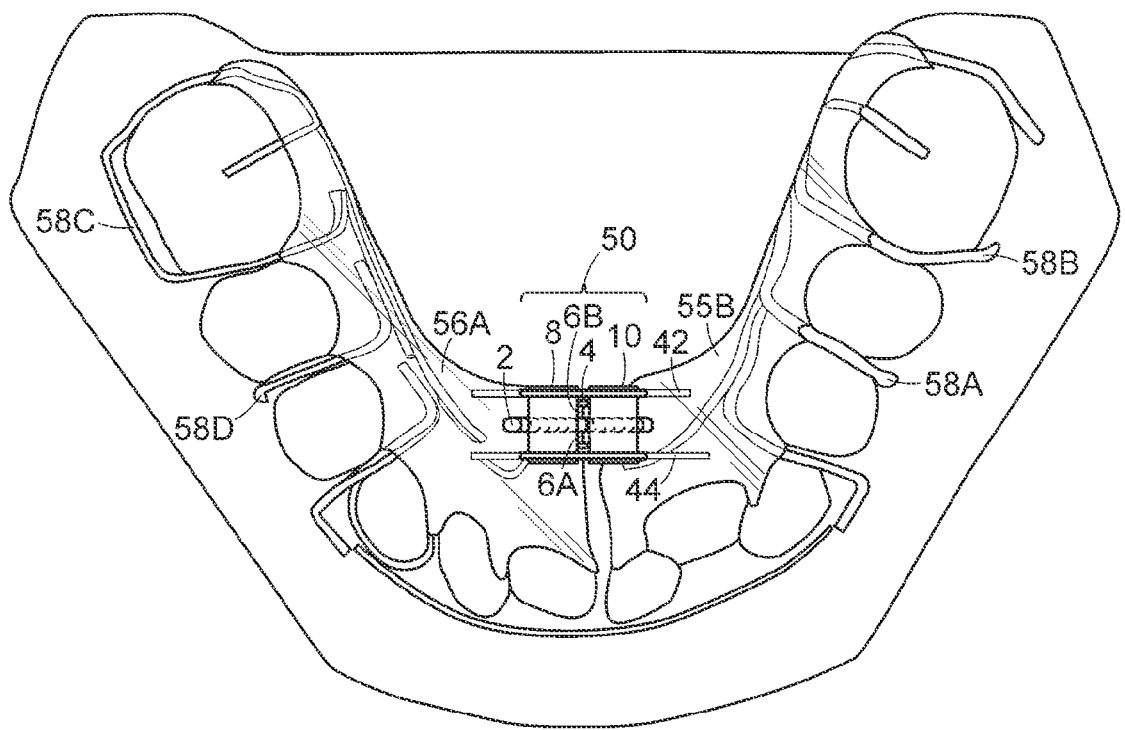
FIG. 8B is a diagram showing an embodiment of the palatal expansion device of the present invention removably secured to a mandible.

Device 50, shown in FIGS. 7, 8A and 8B is similar to that shown in FIG. 6, except that device 50 has no retaining wires. Retaining wires, although used in some embodiments of the invention, are not attached directly to the device in all instances. For example, device 50 can be installed in a patient's mouth with the use of one or more materials that can connect the device to retaining wires or clasps that are secured to teeth. When using clasps, the device is removably secured, similar to a retainer. Such materials and methods for installing them are known in the art. For example, a substance such as acrylic, which is pliable can be used to form fit an impression of the palate and used to connect the device with the retaining wires or clasps that fit the teeth, as shown in FIGS. 8A and 8B. The acrylic in an embodiment can be combined with a monomer that will cause the acrylic to harden. The acrylic support can be formed in one or more plates, and in the embodiment shown in FIGS. 8A and 8B, two plates are used. Alternatively, an impression of the palate can be taken by a dentist or technician and the device and clasps can be connected in a dental lab with similar materials. Acrylic and similar materials are known in the art and can be purchased from Dentaurum (e.g., orthocryl from www.dentaurum.com, DENTAURUM, J. P. Winkelstroeter K G, Turnstraβe 31, 75228 Ispringen, Germany) or Dentsply (e.g., Lucitone from www.dentsply.com, DENTSPLY International, World Headquarters, Susquehanna Commerce Center, 221 W. Philadelphia Street, P.O. Box 872, York, Pa. 17405-0872, USA). Once constructed, the device is held in place by the clasps and the surface contact between the mucosa and the acrylic material. One can use as many clasps or retaining wires as needed to secure the device in proper position. For example, the number of clasps can range from about 1 to about 8. In the embodiment shown in FIGS. 8A and 8B, 6 clasps are used to secure the device.

FIGS. 9A-D show a palatal expander of the present invention that includes a ratchet to achieve unidirectional rotation of the screw. Device 81 employs screw 3 that transects two metal blocks, blocks 9 and 11. Upon activation, screw 3 rotates to push the blocks away from one another. Stabilizing rod 13 is slidably connected to blocks 9 and 11. Blocks 9 and 11 have an opening to receive stabilizing rod 13. Two retaining wires, wires 14C' and 14B', are attached to the blocks at one end and secured to the patient an the other end (not shown). The activator of device 81 involves the use of a ratchet system. As such, ratchet housing 63 houses the ratchet pin and pockets. In addition to providing support for the ratchet system, the ratchet housing protects the oral cavity from inner portions of the ratchet. Ratchet housing 63 is adjacent to housing disk 64 which acts as a wall to the housing and provides support to the housing. Activation arm 7 is attached to the ratchet housing at one end and has circular grip 61 at the other. When the activator is engaged, the ratchet housing rotates along with the screw, and when the activator is returned to its original position, the ratchet housing rotates back to its original position, but screw does not. The inner portions of the ratchet are further described herein.

FIGS. 9A, B, and D show stopper 65 which is attached to ratchet housing 63. When activation arm 7 is pushed downward by the patient, the housing along with the stopper moves along with the activation arm. When the activation is completed and the housing rotates back into its original position, the stopper also rotates. The stopper and the housing continues to move until the stopper hits stabilizing rod 13. In this embodiment, the stopper is a metal stopper, but it can be made from any material so long as the stopper acts to stop the housing from over rotation. A stopper can also be used on the other side of the housing to prevent the activation arm from over rotating in the other direction. A stopper is optional but in certain embodiments is preferable because it assists in providing a consistent activation span. Additionally, structures of the device can also act as a stopper. For example, when the activation arm hits the stabilizer, the stabilizer can act as a stopper in some embodiments.

Figure 9B:
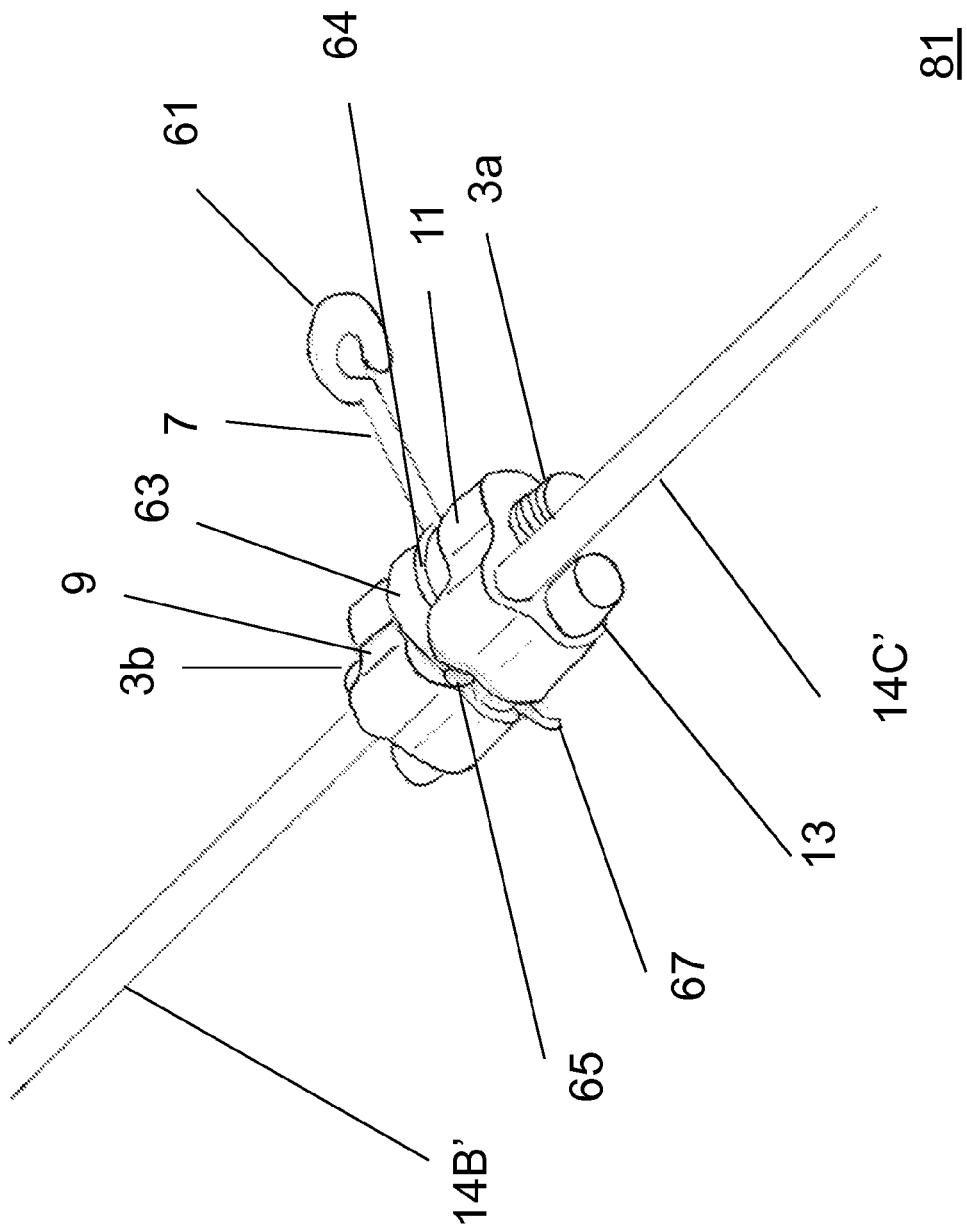
FIG. 9B is a three dimensional drawing of a perspective view of an embodiment of the palatal expansion device having a ratchet system.
Figure 9C:
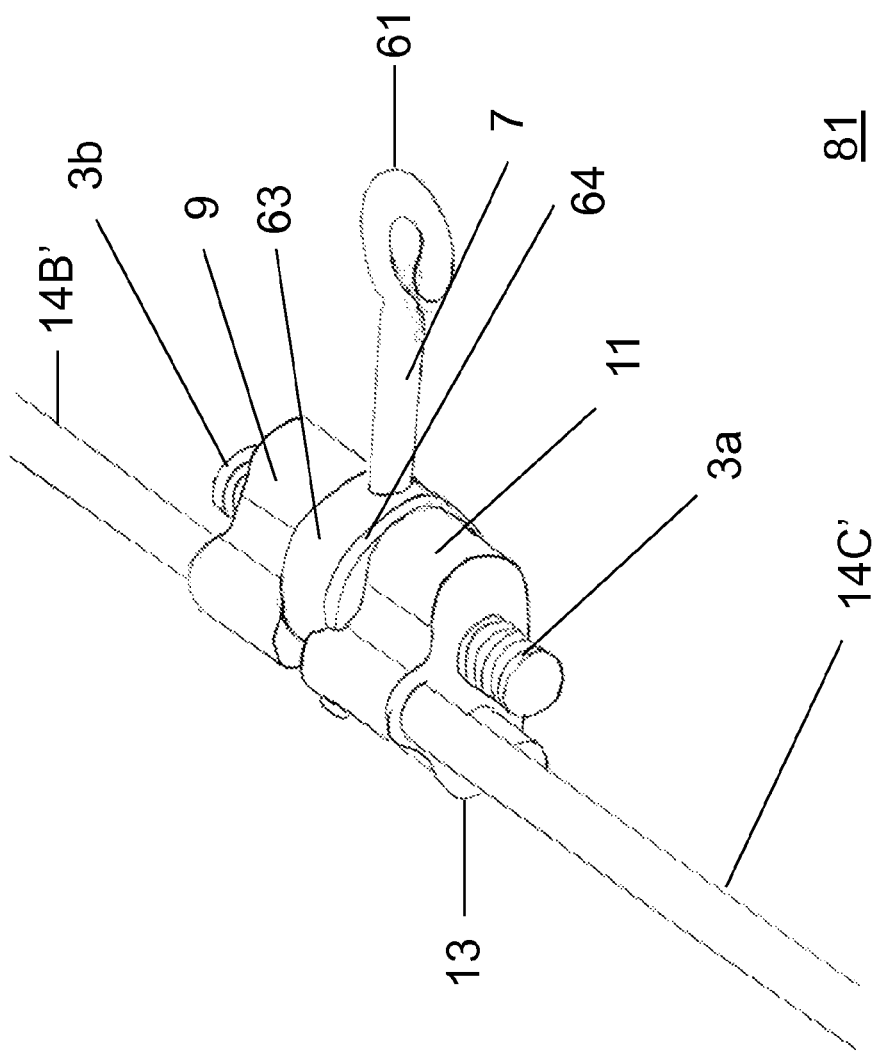
FIG. 9C is a three dimensional drawing of another perspective view of an embodiment of the palatal expansion device having a ratchet system.
Figure 9D:
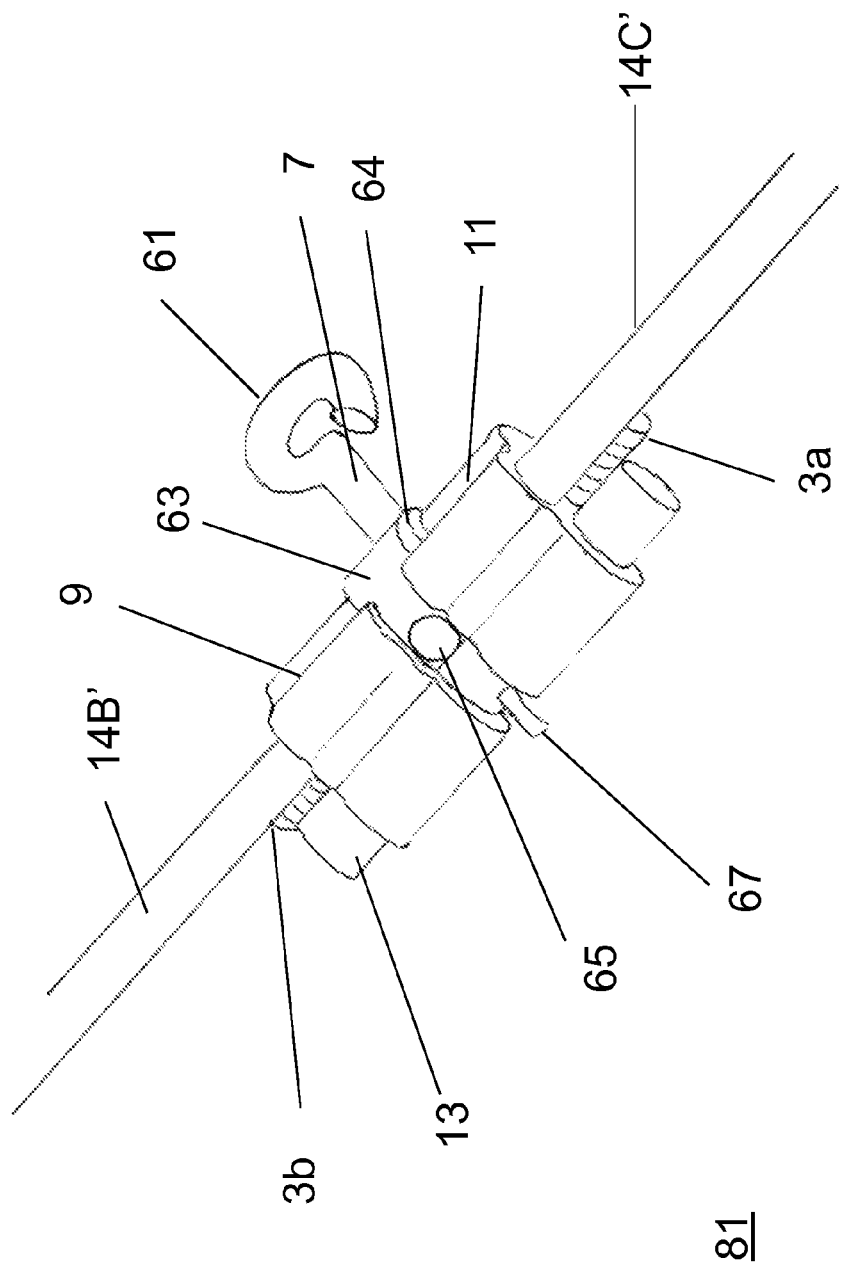
FIG. 9D is a three dimensional drawing of yet another perspective view of an embodiment of the palatal expansion device having a ratchet system.

Overall, device 83 is more compact because it has one stabilizer instead of two, and two retaining wires instead of four. Device 83 has a width (e.g., distance of device when installed that goes from back to front) that ranges between about 5 mm and about 10 mm (e.g., about 7 mm), not including activation arm 7 and circular grip 61, and between about 13 mm and about 20 mm with activation arm 7 and circular grip 61. Other palatal expanders often have a width between about 13 mm and about 14 mm (without the activation arm). The device of the present invention, in an embodiment is up to about 6-7 mm shorter, with an advantage of additional comfort for the patient. A shorter width in achieved, in part by the use of one stabilizer, a ratchet, and positioning of the retaining wires slightly above the screw and stabilizer (FIGS. 9B-D). Positioning certain parts of the expander of the present invention off center (e.g., higher or lower) can provide a more compact expander. For example, rather than positioning the retaining wires off center, the stabilizer or the screw can be positioned off center instead. Positions of various parts of the expander can be modified to obtain a more compact expander.

Figure 10A:
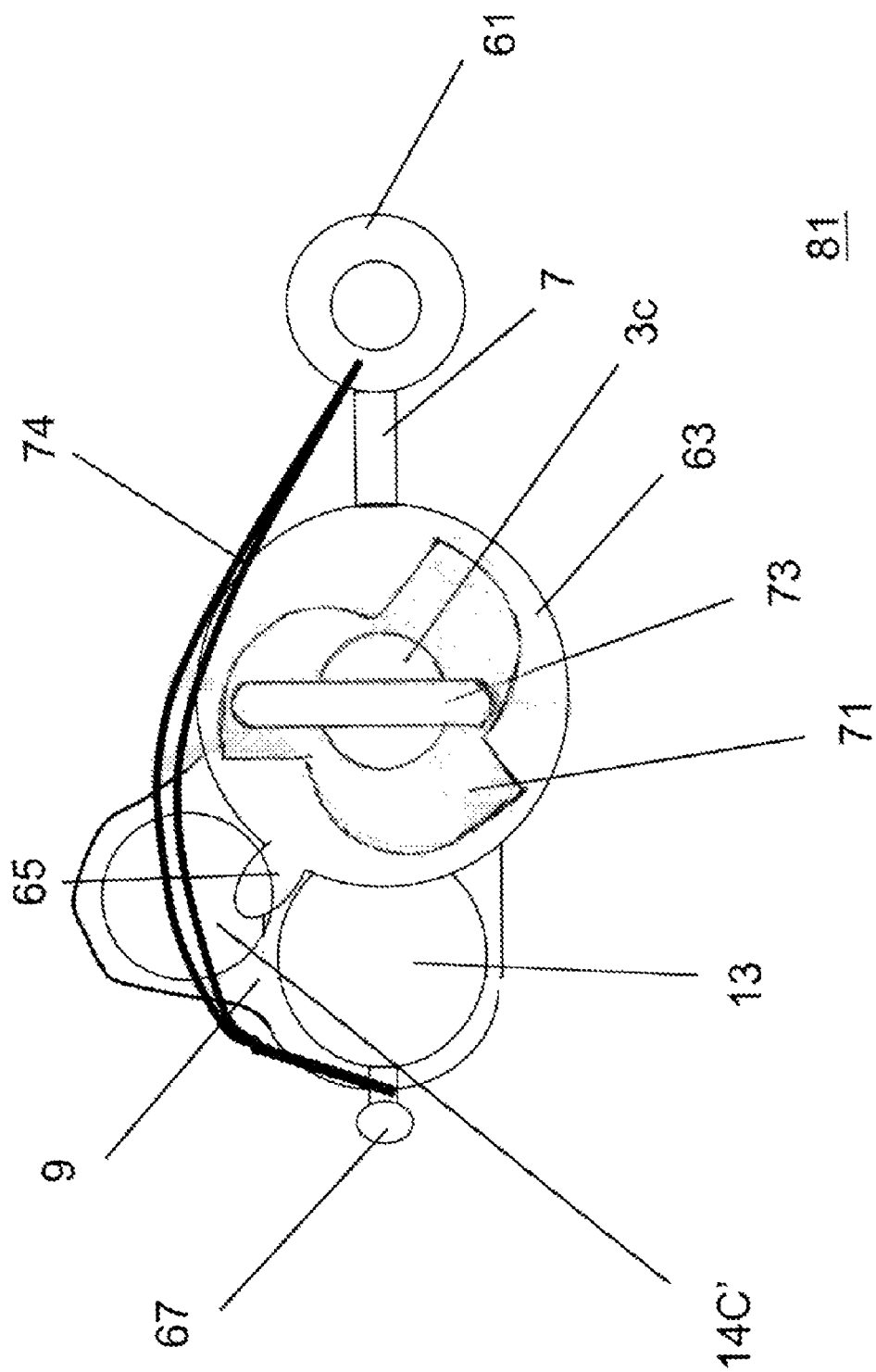
FIG. 10A is a diagram of a cross-sectional view of the palatal expansion device having a ratchet system shown in FIG. 9A.
Figure 13A:
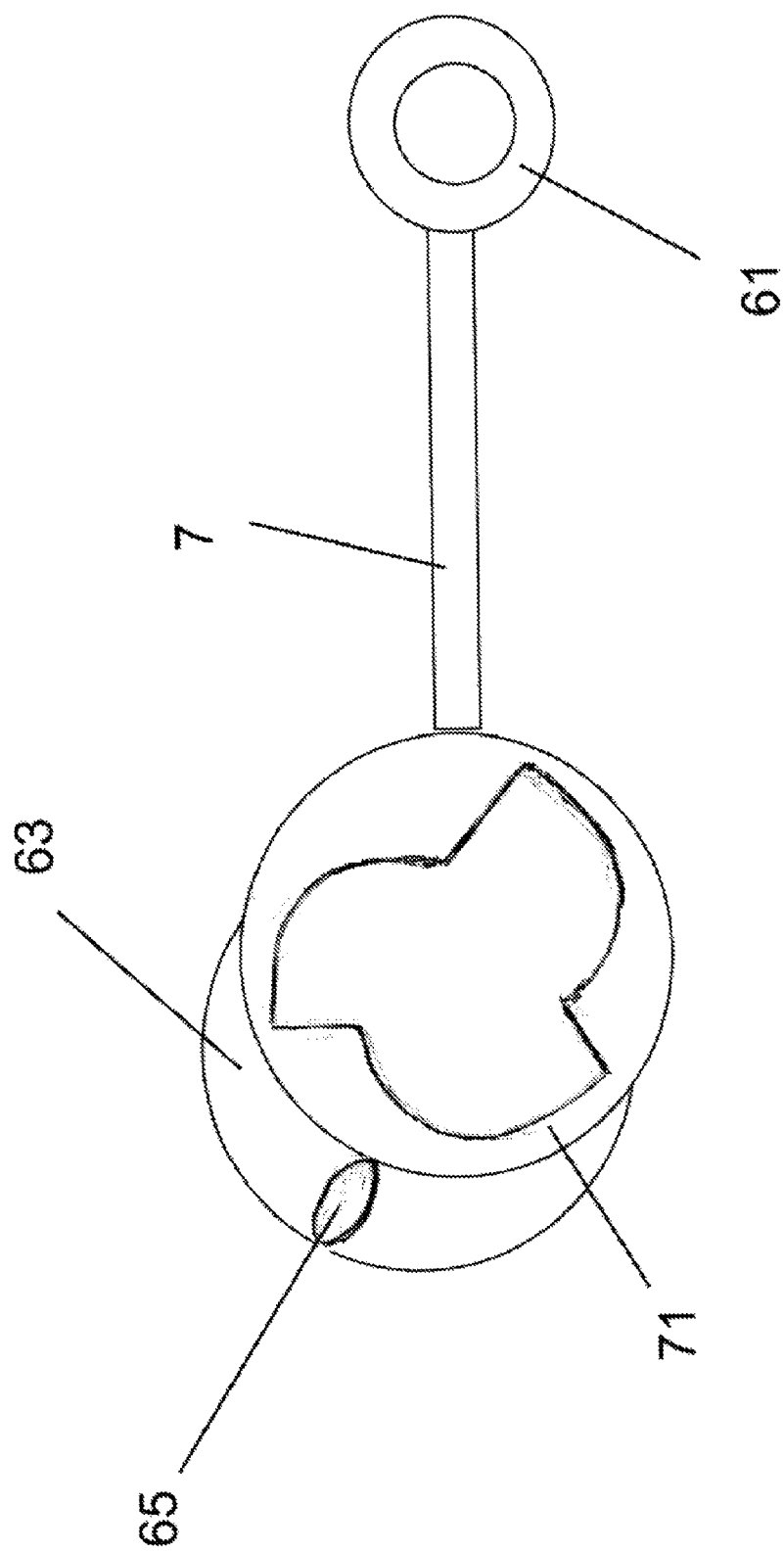
FIG. 13A is a diagram showing the side view of the housing, stopper and activation arm used in an embodiment of the palatal expansion device.
Figure 13B:
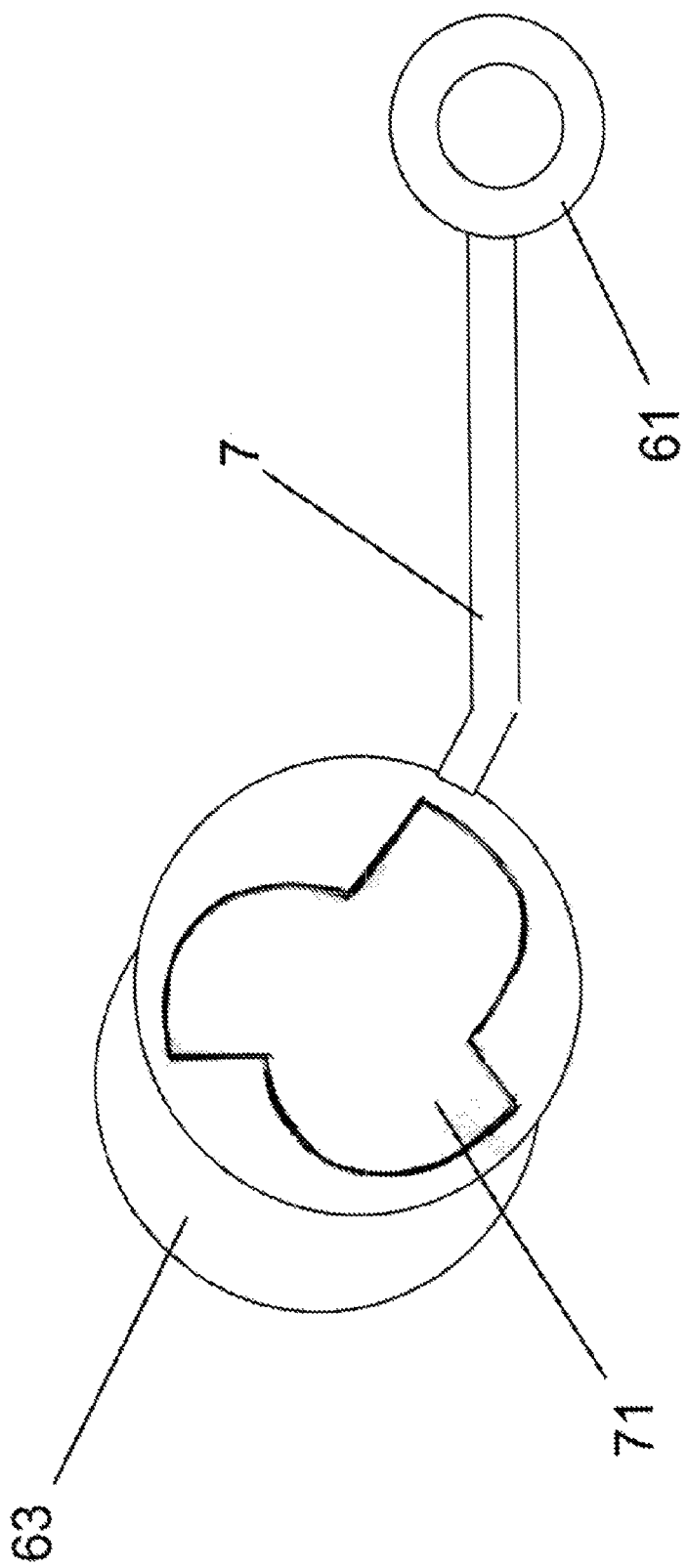
FIG. 13B is a diagram showing the side view of the housing, and activation arm used in another embodiment of the palatal expansion device.

FIG. 10A is a cross section of device 81 and shows the inner workings of the ratchet system. As shown in this figure and FIGS. 13A and 13B, the ratchet includes ratchet housing 63, pin 73 and pocket 71. Pin 73 intersects and slidably connects with screw 3 at 3c. Pocket 71 is made up of three smaller D-shaped pockets that overlap. Each of the three pockets has a straight side and a curved side formed by the inner portion or surface of the housing. The housing and pockets can be made using methods known in the art or developed in the future, and in an embodiment, can use cast metal methods. As activation arm 7 is engaged and ratchet housing 63 turns, so does pin 73. As pin 73 turns, screw 3 also rotates in that same direction. As the activator executes the activation, the screw goes from a first position (e.g., the starting position) to a second position (e.g., the ending position). Once the activator completes the activation and as it beings to return to the staring position, the pin slides along the curved portion of the inner housing. The curved edge of the inner house serves to push the pin downward into another smaller pocket. The curved inner portion of the housing continues to push the pin until the pin rests against a straight side of another pocket, and is ready for the next activation. As such, when the arm is being returned to its starting position, the screw is not engaged and is not unwound (e.g., wind-back is prevented). Rather, the pin serves to prime the ratchet for the next activation. The length of the pin and the number and shape of the pockets can vary, and can depend one another. A ratchet system with a shorter pin can include more pockets (e.g., 4 pockets instead of three). Also, the radius of the pocket curve can be modified as well. A smaller radius can result in more pockets, and a larger radius can result in less pockets. For example, the present invention includes a ratchet housing having about 2, 3, or 4 pockets. Another factor that can affect the number of pockets and length of the pin is the rotation that one wants to achieve with a single activation. The current embodiment with 3 pockets allows for a 120 degree activation, whereas an embodiment with 4 pockets provides a 90 degree activation. A 2 pocket embodiment would allow for a 180 degree activation. The amount of rotation is dependant on the width of the screw, the amount of activation desired, as further described herein.

Figure 17A:
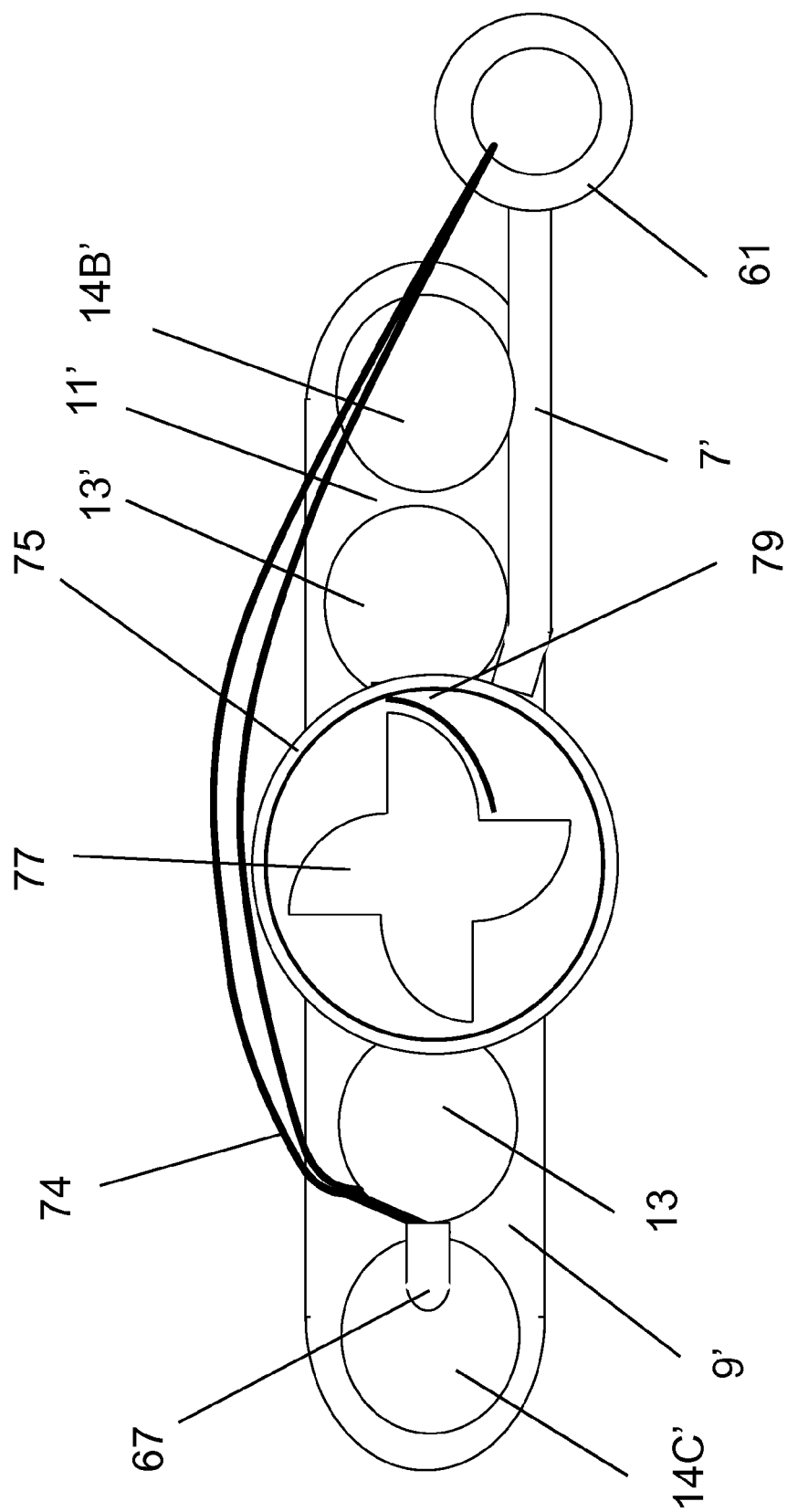
FIG. 17A is a diagram of a cross-sectional view of the palatal expansion device having a ratchet system using a ratchet wheel.
Figure 17B:
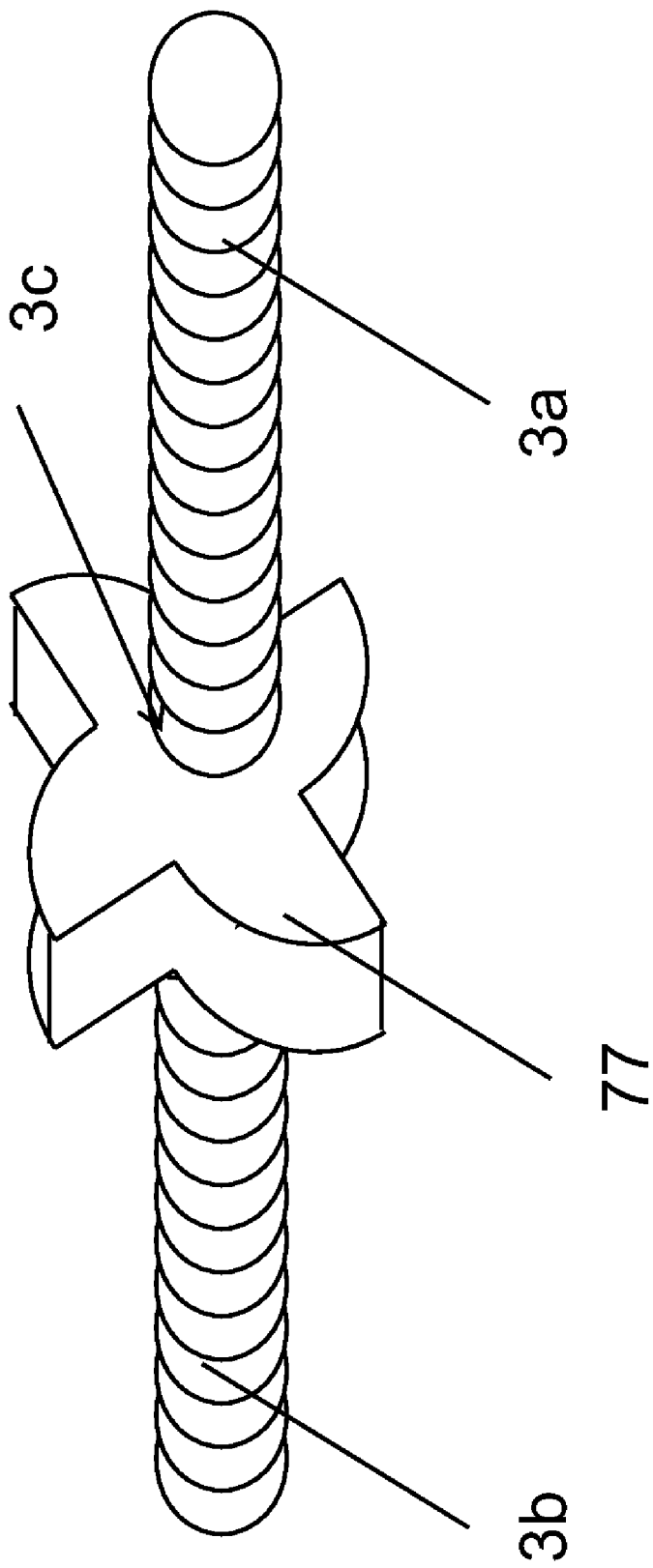
FIG. 17B is a diagram showing the side view of a screw used in an embodiment of the palatal expansion device of FIG. 17A.

Other ratchet systems can be employed to achieve unidirectional rotation of the screw. For example, a ratchet wheel with a series of projections or teeth can be used opposite a pawl, spring extension, plate or curtain. Teeth or projections can be angled or shaped to facilitate the unidirectional rotation. Similarly, the device opposite the teeth can also be angled or shaped to direct unidirectional flow and prevent wind back. The projections and the device opposite the projections can complement one another to allow unidirectional rotation. Such an embodiment is shown in FIG. 17A and is further described herein. Any ratchet systems known or developed in the future can be used to achieve unidirectional rotation of the screw in the palatal expander of the present invention.

Figure 10B:
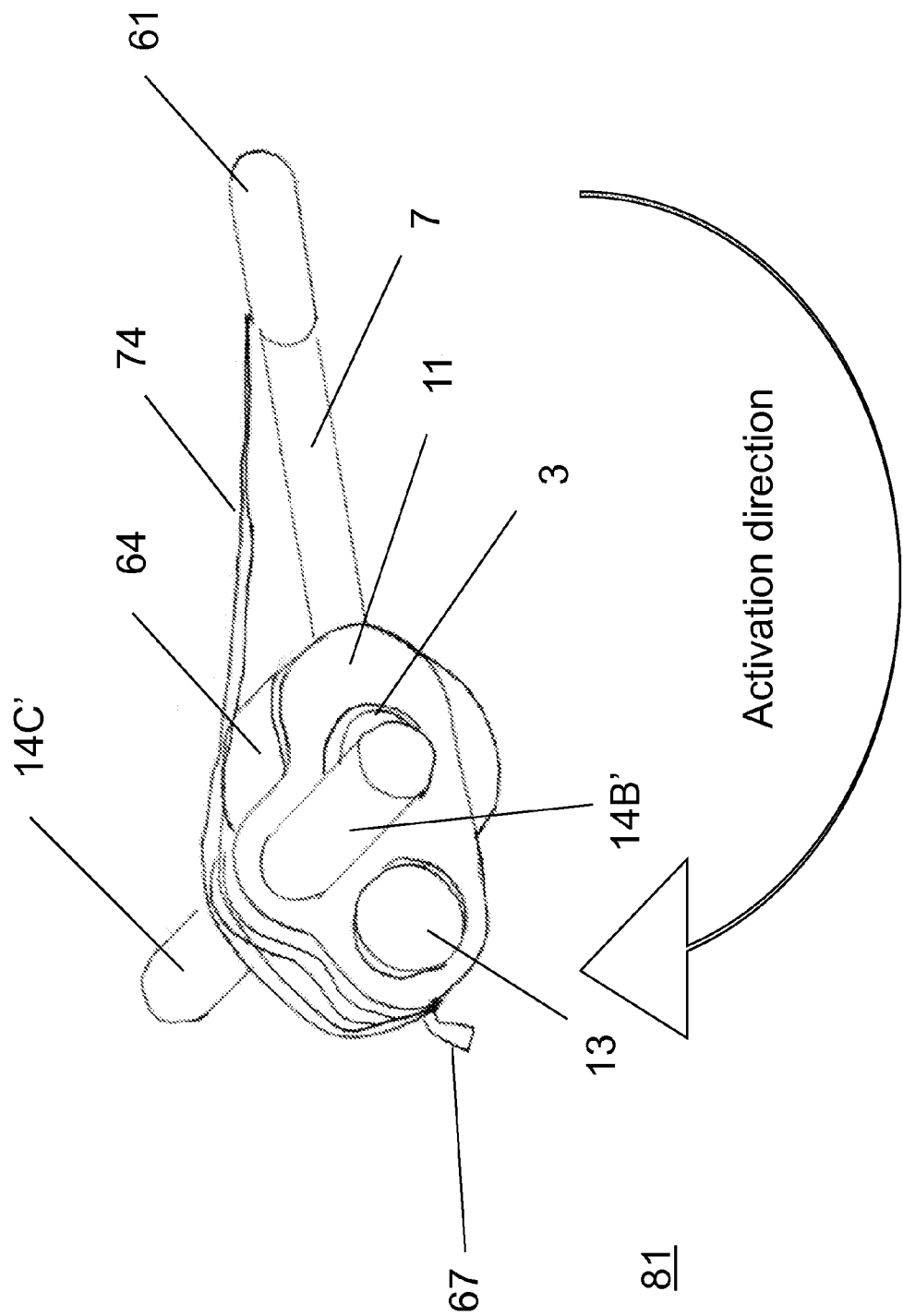
FIG. 10B is a three dimensional drawing of a cross-sectional view of the embodiment of the palatal expansion device having a ratchet system shown in FIGS. 9A, B, C, and D.

FIGS. 10A and 10B also include hook 67 attached to stabilizing rod 13. The hook is an anchor for a pull back device that engages the activator. Other than a hook, any projection can be used to serve as an anchor. Examples of anchors include hoods, protrusions, rings, extensions, and the like. Additionally, structures that are already part of the palatal device of the present invention can further act to serve as an anchor of the pull back device. As such, an additional structure used as an anchor is optional. In an embodiment, the pull back device can be any device that allows the activator to recoil or spring back into the starting position, and includes elastic members. Examples of elastic members include elastic thread, elastic chain, or coil spring. Elastic members known or later developed can be used to pull back the activator back into its starting position. The elastic member is tied or attached to the hook, and also secured to engage the activator. In FIG. 10B, elastic member 74 is tied to base of circular grip 61 to engage activation arm 7. However, the elastic member can be attached to any portion of the grip, the activator, the housing or a structure on the housing such as the stopper to pull back the activator into starting position. In an embodiment, the activator can be placed back into starting position by the user or the dentist, rather than done automatically with the pull back device.

FIG. 11 shows stabilizing rod 13 of device 81. As described herein, any stabilizer can be used and includes bars, prisms, and the like. Stabilizers can be primarily of any shape and can have indentations to receive other portions of the palatal expanding device. Stabilizing rod 13 has indent 69 shaped to receive ratchet housing 63 and housing disk 64. Rather than using indentations to receive portions of the housing, rings or disks can be used to keep the housing in place. Any device or mechanism known in the art can be used to keep the housing in place. Like the stabilizing rod, any portion of the palatal expander of the present invention can be modified to receive other portions of the expander. Another such example include the blocks, which can be shaped to receive the housing or the retaining wires. Having portions of certain pieces cut away to receive another piece of the device allows the device, in part, to be more compact yet still perform the same function.

Figure 12:
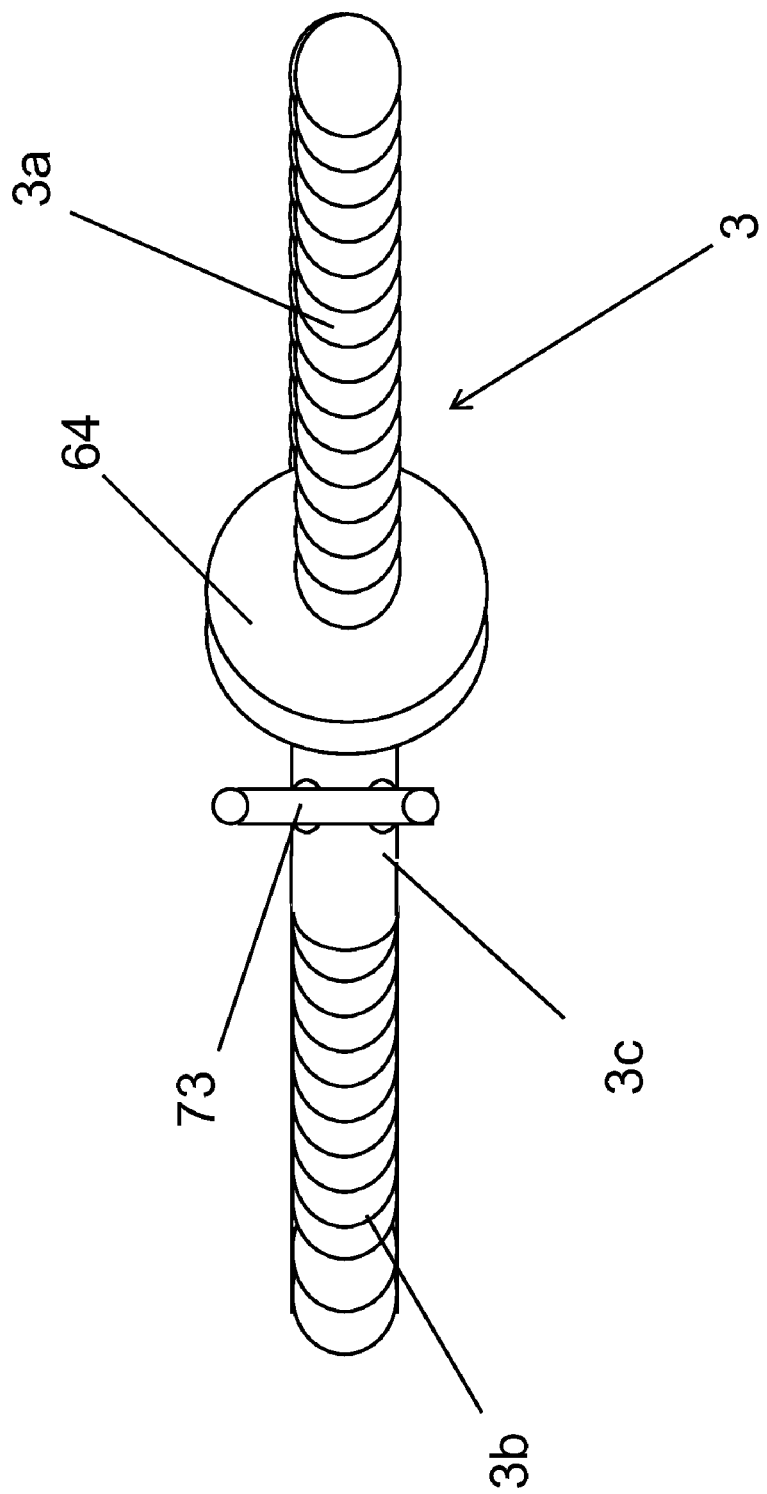
FIG. 12 is a diagram showing the side view of a screw used in an embodiment of the palatal expansion device.

Referring to FIG. 12, screw 3 is shown. Portions 3*a* and 3*b* of screw 3 are joined at center portion 3*c*, which in an embodiment was soldered together. Center portion 3*c* has an opening to slidably receive pin 73. Center portion 3*c*, in an aspect, can be rounded or rectangular. Pin 73 is can move up and down the opening in portion 3*c*. Screw 3 also has housing disk 64 attached thereto. When ratchet housing 63 is slid over portion 3*b* to be attached to the screw assembly, housing disk 64 acts to form a side of the housing so that the oral cavity (e.g., the tongue) is protected from the pin and ratchet pockets. The disk also acts to provide support to the housing to keep it in place during use. One or more disks, walls, or plates can be used. Preferably, the disks, walls or plates used to keep the housing in place complements the shape of the housing. Since pin 73 is slidably integrated with the screw, the pin causes rotation of the screw while still being able to slide within the pockets as described herein. The ratchet housing can be of any shape so long as it provides protection from the internal mechanisms of the ratchet, and/or provides support for the ratchet system. Although the ratchet housing 63 along with housing disk 64 provides both protection and support, in some embodiments the ratchet system does not have to be fully covered. As such, the housing disk 64 is optional in some embodiments.

Activation arm 7 of device 81, attached to the ratchet housing can be shaped and have characteristics of other embodiments already described herein. The activator can be attached directly to the housing via soldering, or screwed into the housing. The housing can also include a track into which an arm with a plate can be locked into place. Additionally, the activation arm can be straight, or angled in one or more places. A longer activation arm requires less force by the patient to activate the expander, and so it is easier for the patient to activate the screw. Activation arm 7 in FIG. 13A begins at circular grip 61 and extends straight to the housing, whereas in FIG. 13B activation arm 7' is angled by about 45 degrees at one point. Angling the activation arm, in certain embodiments, allow the arm to be tucked out of the way.

Figure 16:
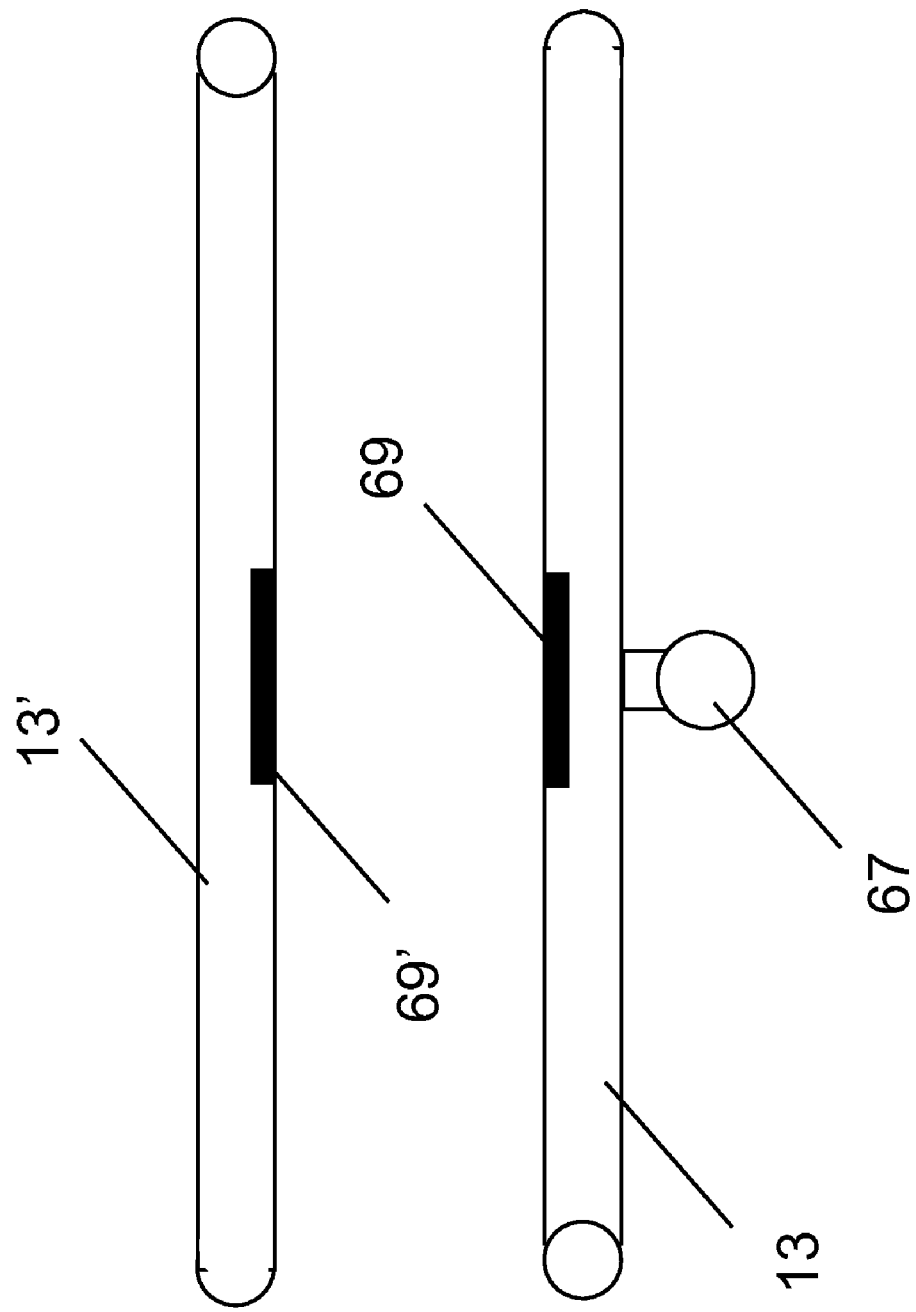
FIG. 16 is a diagram showing the top view of stabilizers used in an embodiment of the palatal expansion device.

In FIG. 14, device 83 is another embodiment of the palatal expander with a ratchet, however, device 83 includes two stabilizers, stabilizers 13 and 13', and four retaining wires, wires 14A', 14B', 14C' and 14D'. Device 83, as compared with device 81, has a larger overall width and can be used in the case where the patient has a larger oral cavity, or where additional support may be needed (e.g., a male adult) for the expansion to occur (e.g., more force is required). The additional stabilizers provide more support for blocks 9' and 11'. Block 9' and 11' are adapted to slidably receive both stabilizers which allow the blocks to expand upon activation. Furthermore, the stabilizers act as a stopper to indicate the starting and stopping position for the activation arm. The blocks also have two additional retaining wires attached thereto. Stabilizers 13 and 13' are modified with an indentation to receive ratchet housing 63 and housing disk 64. See FIG. 16.

Figure 15:
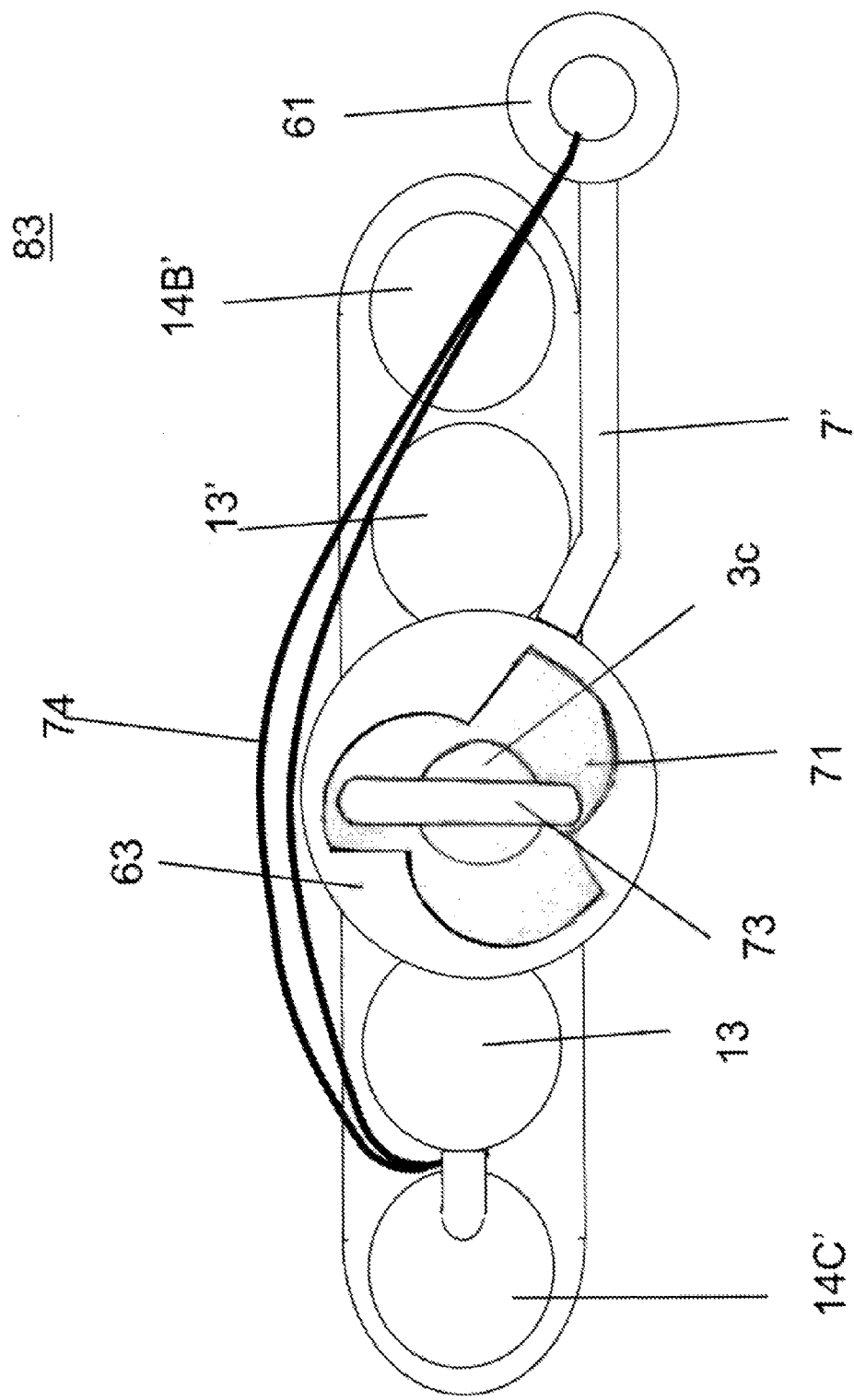
FIG. 15 is a diagram of a cross-sectional view of the palatal expansion device having a ratchet system shown in FIG. 14.

FIG. 15, showing the cross-sectional view of device 83, shows the same ratchet system as that of device 81. The cross sectional view show additional stabilizer 13' and retaining wire 14B'. A notably modified feature is angled activation arm 7'. The addition of the stabilizer and retaining wires causes the overall width of the device to be greater. As such, activation arm 7' is also longer so that the patient can get access to it. The arm is angled so as to keep it out of the way e.g., away from the tongue. The angled activation arm is optional, but in this case preferable. The rest of the features of the expander are similar to device 81, which have been described herein.

Figure 18:
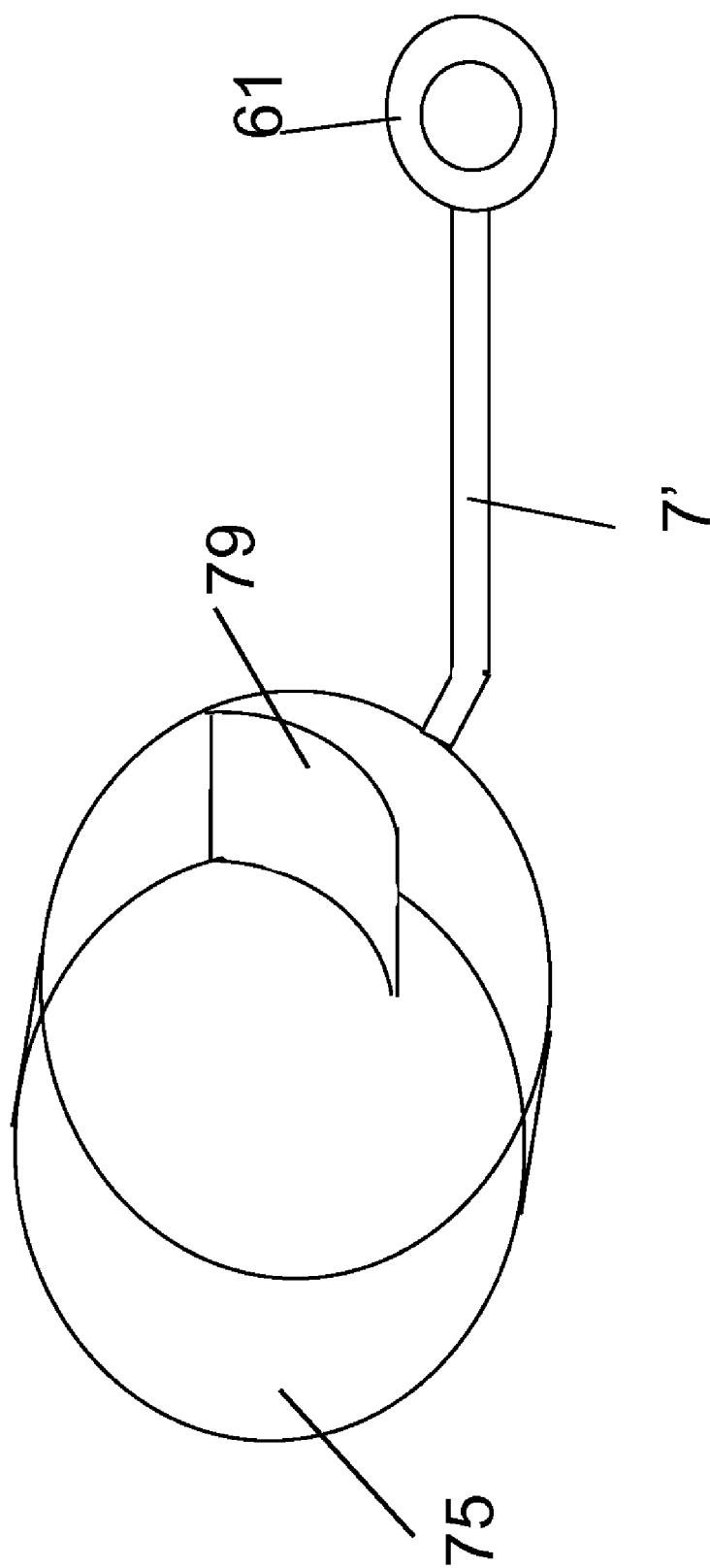
FIG. 18 is a diagram showing the side view of the housing, stopper and activation arm used in an embodiment of the palatal expansion device.
Figure 19:
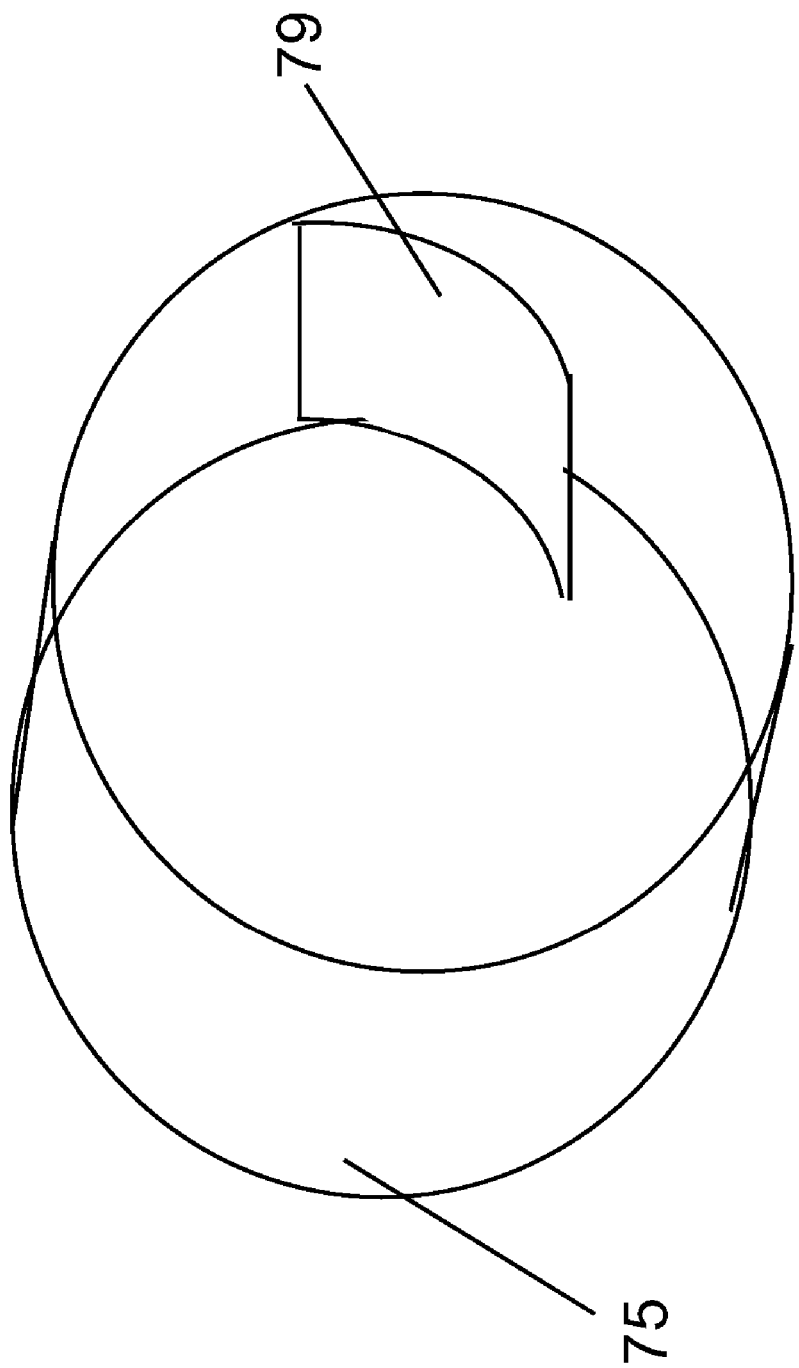
FIG. 19 is a diagram showing the side view of the housing, and curtain used in an embodiment of the palatal expansion device.
Figure 20:
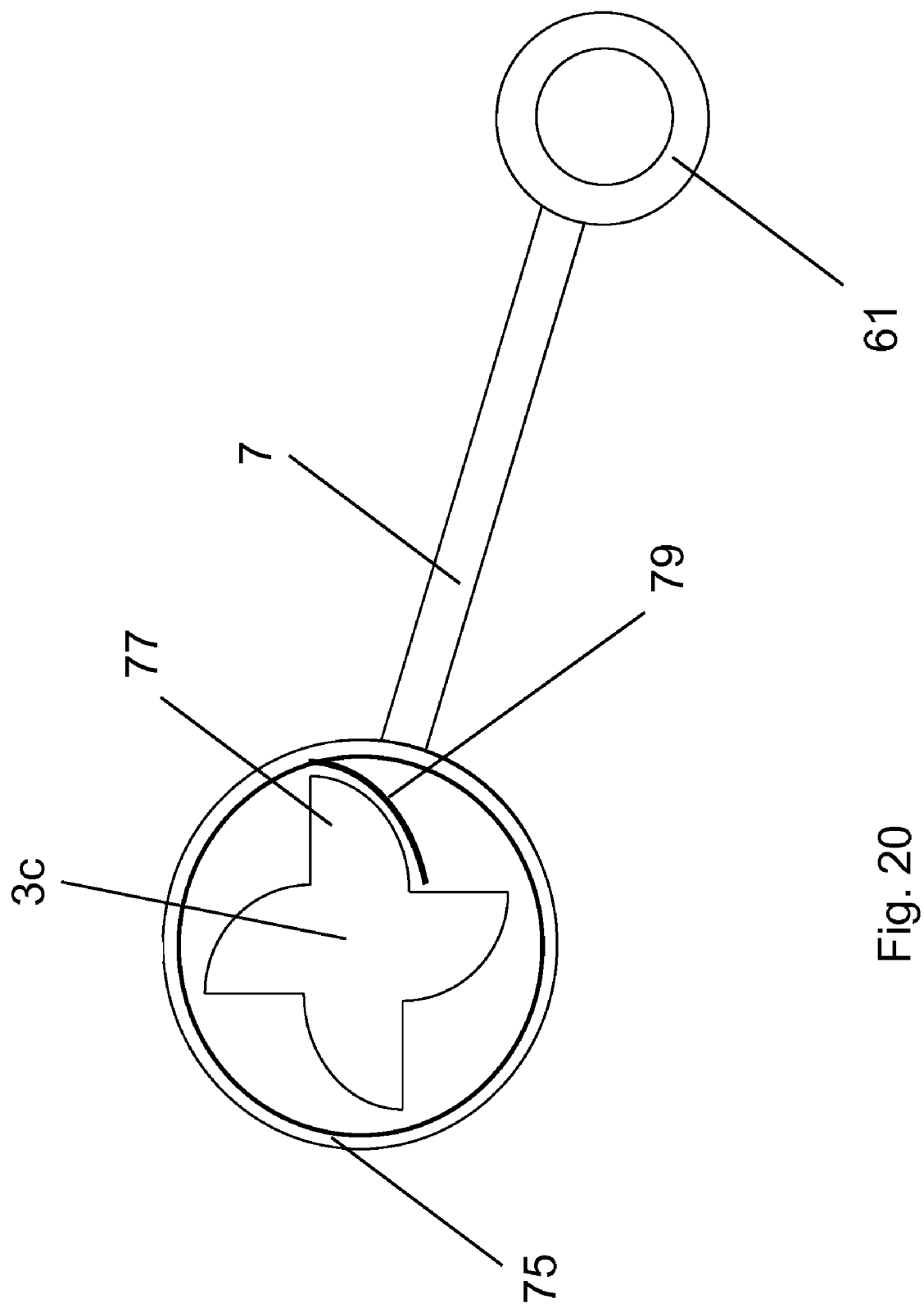
FIG. 20 is a diagram showing the side view of the housing, the ratchet wheel, the stopper and activation arm used in an embodiment of the palatal expansion device.

FIGS. 17A, 17B, 18, 19, and 20 illustrate another ratchet system that can be employed by the present invention. This ratchet system involves ratchet wheel 77 having four protections. Each projection has a partial "D" shape with a straight line and a curved line. There can be a plurality of protections, each shaped to facilitate unidirectional rotation of the screw. Ratchet wheel 77 is attached to screw 3 at portion 3*c*. See FIG. 17B. The projections can have any shape, size and/or thickness so long as they allow for unidirectional rotation of the screw. The projections can be angled to allow rotation in one direction and prevent or make more difficult a rotation in the opposite direction. The ratchet system shown in device 85 also includes housing 73 and curtain 79. Curtain 79 is angled and uses the straight edge of the projection to engage the screw, and the curved edge of the projection to passively retract the arm to prevent windback. FIG. 20 shows a cross-section of the ratchet system and FIGS. 18 and 19 show housing 73. As such, when activation arm 7' is engaged, housing 75 along with curtain 79 moves in the activation direction. During activation, curtain 79 engages the straight edge of the projection and rotates the screw until it reaches the end of the activation span. When the activation arm goes back to the starting position, curtain 79 passes the curved edge of the adjacent projection and slides past the projection without rotating the screw. When stopper 65' hits the stabilizing bar, the activation span is completed and the arm can be returned to its original position. See FIGS. 18 and 20. In addition to a curtain, the spring can be an extension, or a plate. Various types of springs or spring extensions, and materials from which they can be made have been described herein. In yet another embodiment, the ratchet teeth can be on discs or gears that interlock and allow unidirectional rotation.

The present invention also includes methods for expanding the maxillary arch or mandible. The steps of the method include securing the device, as described herein, to the maxillary arch or mandible (e.g., to the molar and premolar bands), and engaging the activation arms (e.g., turning the activation arm). Securing the device to the maxillary arch or mandible involves positioning or aligning the device and securing the retaining wires to the pre-molar bands. In the case in which the device does not have retaining wires directly attached to it, the steps of the method include taking an impression and form fitting the device into the hardened impression using material such as acrylic and inserting a means of attachment (e.g., clasps). In general, palatal expansion therapy affects craniofacial structures and the teeth onto which the appliance is adapted. In the horizontal plane, the midpalatal suture separates asymmetrically in a "V"-shaped pattern, with the greatest expansion occurring in the anterior aspect of the palate. Data indicates that the greatest resistance to sutural splitting is in the posterior aspect of the palate, because of the articulation of the maxilla with the surrounding cranial bones, such as the zygomatic buttress. These anatomic considerations result in the above-mentioned pattern of expansion with any tooth-borne appliance. Therefore, in one embodiment the device is placed near the sources of anatomic resistance such as the zygomatic buttresses. Such placement causes a more uniform pattern of palatal expansion. As shown in FIG. 8B, the placement of the device in the mandible differs somewhat from that in the maxillary arch. When placing or aligning the device in the mandible, the device is generally aligned closer to the front of the mouth and angled to avoid the tongue.

As described herein, the methods of the present invention include activation that occurs on a daily basis (e.g., once a day, twice a day, or three times a day), every other day, or a few times a week. The device can be used for a rapid expansion or a slow expansion, depending on the patient's condition and desired expansion. In one example of a rapid expansion, activation occurs twice a day by turning the activation arm downward and backward wherein every activation is 0.25 mm. The patient can activate the device with the help of the index finger until it clicks. In the case of a slow expansion, activation occurs about once to twice per week. At the time that the activation arm clicks, the activation arm disappears and hides between the metal blocks and does not irritate the tongue. The activation occurs until the desired expansion is obtained, e.g., between about 7 mm and about 11 mm. In one aspect of the invention, the period for rapid expansion is between about 1 and about 2 weeks, and the period for slow expansion is from about 1 month to about a year, and preferably between about 6 to 8 months. The expansion period can be followed by a stabilization period (e.g., about 3 months for rapid expansion and about 1 year for slow expansion), where the maxillary arch or mandible acclimates to the expansion. The spring extension, ratchet system, or similar anti-windback mechanism, as described herein, prevents the screw from unwinding and maintains the expansion.

In another embodiment of the present invention, the device described herein is activated independent of an expansion key. More specifically, the device is activated by the patent by engaging the activator, or alternatively can be activated by a battery powered or wind-up mechanism. For example, time can be kept using oscillation that is provided by a wound spring through a set of gear wheels (the wheel train). The spring of the mechanism can be wound periodically (e.g., every few days) by the patient or by a battery. Technology, such that used in Swiss or battery operated watches, can be adapted and used with the device of the present invention.

The present invention also relates to a kit including the device, as described herein, acrylic or similar materials, two or more clasps, and/or two or more retaining wires. Optionally any other tool or items used to secure the device to the maxillary arch or mandible, or to activate the device can also be included.

EXEMPLIFICATION

Anti-windback palatal expander device with 4 activation arms:

The palatal expansion device shown in FIG. 1 was made with the following specifications. The device was made with 2 metal blocks and a metal screw having a tread of 2 mm, and a length of either 7 mm, 9 mm or 11 mm. Each metal block had an opening to receive and complement the screw, and the opening ran the entire length of the screw. The screw had 4 activation arms attached to the center, each arm positioned to cause the screw to turn a ¼ of a turn. Each activation arm had a ball-like protection at its end. The screw of the device together with the activation arms work like a sprocket wheel. The device was made for activation that occurs twice a day, with every activation being 0.25 mm. The device also had a stabilizing bar which was a square shaped prism that went through the square shape holes of the blocks. Attached to the stabilization bar was a spring extension that acted as a self-locking or anti-wind back mechanism for screw. The spring extension, that was made from a nickel titanium alloy, looked like a plate projection that functions like a cog to lock the screw. The device had 4 retaining metal wires, wherein 2 wires were attached to each metal block.

A number of patients wore this device and activated it with their index finger until it clicks. At the time that the arm clicks, the activation arm disappears and hides between the metal blocks and does not irritate the tongue. The period for expansion was between about 1 and about 2 weeks. If further expansion was needed, a second, longer screw was used for a period of about 1 to about 2 additional weeks (e.g., about 3 or 4 weeks total). The expansion period was often followed by a stabilization period (e.g., about 3 months), where the maxillary arch acclimated to the expansion.

Palatal Expander with Ratchet System:

The palatal expansion device shown in FIGS. 9A and 14 were made with the following specifications. The device were made with 2 metal blocks and a metal screw having a tread of 2 mm, and a length of either 7 mm, 9 mm or 11 mm. Each metal block had an opening to receive and complement the screw, and the opening ran the entire length of the screw. The ratchet system was made using 3 winged-shaped pockets, a pin, and a ratchet housing. The housing disk was placed on the screw, and the pin was inserted into two holes in the middle of the screw. The ratchet housing was slid over the screw until the pin sat inside the housing and the housing met with the disk. The activation arm having a circular grip was soldered onto the housing. For the device shown in FIG. 9A, a single stabilizing rod was inserted into the block, and for the device of FIG. 14 two stabilizing rods were inserted. Retaining wires were soldered onto the blocks, as shown in the figures.

The ratchet, upon activation, rotated the screw when the arm was moved from the starting position to the ending position. When the arm is returned to the ending position, the housing passively slides past the ratchet mechanisms and does not engage the screw. Both expansion devices included a stopper on the housing to indicate when to stop activation, and a hook so that the orthodontist can place an elastic member such as a coil chain to facilitate pull back of the arm automatically.

The device in FIG. 14 was placed in a patient for several weeks. The patient engaged the activation arm daily to effectuate a 120 degree rotation. The arm automatically pulled back into starting position using the coil spring. The period for expansion was about 2 weeks and desired expansion was achieved. The expansion period was followed by a stabilization period of about 3 months, where the maxillary arch acclimates to the expansion. Photographs were taken of the palatal expander installed on the patient.

The relevant teachings of all the references, patents and/or patent applications cited herein are incorporated herein by reference in their entirety.

While this invention has been particularly shown and described with references to preferred embodiments thereof, it will be understood by those skilled in the art that various changes in form and details may be made therein without departing from the scope of the invention encompassed by the appended claims.

What is claimed is:

1. A palatal expansion device comprising:
   a. at least one screw, wherein the screw connects with at least two blocks, the block having an opening for receiving the screw;
   b. one or more stabilizers attached to the blocks;
   c. a built-in activation arm attached to a ratchet housing, wherein the ratchet housing comprising one or more pockets to guide movement of a pin, wherein
   the pin, slidably transects the screw, at the one or more pockets;
   d. a ratchet housing disk attached to the housing to thereby enclose the pin and the one or more pockets; and
   e. an elastic member, secured to the activation arm and to any component of the device including the stabilizer or one of the blocks, to retract the activation arm after activation;
   wherein, when activated, the activation arm engages the ratchet housing having the pin, the pin engages the screw, and the screw moves the one or more blocks, to thereby allow essentially unidirectional rotation of the screw.

2. The palatal expansion device of claim 1, wherein the ratchet housing has three pockets in communication with one another and shaped to guide movement of the pin, wherein each pocket is shaped with a straight edge and a curved edge.

3. The palatal expansion device of claim 2, wherein the screw has an opening to slidably receive said pin.

4. The palatal expansion device of claim 2, wherein the straight edge of the pocket engages the pin to turn the screw.

5. The palatal expansion device of claim 4, wherein the curved edge of one pocket engages the pin to slide into another pocket without turning the screw.

6. A palatal expansion device comprising:
   a. at least one screw, wherein the screw connects two blocks, the blocks having an opening for receiving the screw, wherein the screw has an opening to receive a pin;
   b. one or more stabilizers attached to the blocks;
   c. a built-in activation arm attached to a ratchet housing, wherein the ratchet housing comprising one or more pockets shaped to guide movement of the pin, wherein
   the pin, slidably transects the screw, at the one or more pockets; and
   d. a pull back device, secured to the activation arm and to any component of the device including the stabilizer or one of the blocks to retract the activation arm after activation, wherein the pull back device is an elastic member;
   wherein, when activated, the activation arm engages the ratchet housing having the pin, the pin engages the screw, and the screw moves the two blocks, to thereby allow the screw to move from a first position to a second position and the screw is prevented from moving back to the first position.

7. The palatal expansion device of claim 6, wherein the elastic member comprises a spring coil, elastic thread, elastic chain, or combination thereof.

8. The palatal expansion device of claim 6, further including two or more retaining wires for securing the appliance to teeth, said wires are laterally attached to said blocks.

9. The palatal expansion device of claim 6, wherein the screw essentially perpendicularly transects said blocks at the opening.

10. A palatal expansion device comprising:
    a. two blocks:
    b. a separator for separating the two blocks;
    c. a stabilizer for stabilizing said blocks;
    d. a ratchet housing between the two blocks, wherein the ratchet housing comprising one or more pockets shaped to guide movement of a pin, wherein the pin slidably transects the separator, at the one or more pockets;
    e. a built-in activation arm attached to the ratchet housing; and
    f. an elastic member, secured to the activation arm and to any component of the device including the stabilizer or one of the blocks, to retract the activation arm after activation;
    wherein, when activated, the activation arm engages the ratchet housing having the pin, the pin engages the separator, and the separator moves the two blocks, thereby allowing essentially unidirectional rotation of the separator while preventing retraction of said blocks.

11. The palatal expansion device of claim 10, wherein the stabilizer comprises a bar, a prism, or a rod securely attached to said blocks.

12. The palatal expansion device of claim 10, further including two or more retaining wires for securing the appliance to teeth, said wires are laterally attached to said blocks.

13. A method of expanding a maxillary arch or mandible of a person, said method comprises the steps of:
    a. securing a palatal expansion device in the maxillary arch or mandible of said person, wherein the device comprising:
       i. at least one screw, wherein the screw connects with at least two blocks, the block having an opening for receiving the screw;
       ii. one or more stabilizers attached to the blocks;
       iii. a ratchet housing at the blocks, wherein the ratchet housing comprising one or more pockets shaped to guide movement of a pin, wherein the pin slidably transects the screw at the one or more pockets;
       iv. built-in activation arm attached to the ratchet housing; and
       v. an elastic member, secured to the activation arm and to any component of the device including the stabilizer or one of the blocks to retract the activation arm after activation;
       wherein, when activated, the activation arm engages the ratchet housing having the pin, the pin engages the screw, and the screw moves the one or more blocks, and
    b. engaging the built-in activator to thereby expand the arch.

14. The method of claim 13, further including engaging the activator periodically.

15. The method of claim 14, wherein the activator is engaged daily for a period of between about 1 week and about 2 weeks.

16. The method of claim 14, wherein the activator is engaged once or twice a week for a period of between about 2 months and about 1 year.

17. A kit for palatal expansion that comprises:
    a. palatal expansion device having:
       i. at least one screw, wherein the screw connects with at least two blocks, the block having an opening for receiving the screw;
       ii. one or more stabilizers attached to the blocks;
       iii. a ratchet housing at the blocks, wherein the ratchet housing comprising one or more pockets shaped to guide movement of a pin and houses the pin, wherein the pin, slidably transects the screw, at the one or more pockets;
       iv. a built-inactivation arm attached to the housing; and v. an elastic member, secured to the activation arm and to any component of the device including the stabilizer or one of the blocks to retract the activation arm after activation;

wherein, when activated, the activation arm engages the ratchet housing having the pin, the pin engages the screw, and the screw moves the one or more blocks, and to thereby allow essentially unidirectional rotation of the screw; and b. two or more retaining wires for securing the appliance to teeth, said wires are laterally attached to said blocks.

18. The kit of claim 17 further including four retaining wires.

* * * * *